US012378527B2

(12) United States Patent
Tryggvason et al.

(10) Patent No.: US 12,378,527 B2
(45) Date of Patent: *Aug. 5, 2025

(54) DIFFERENTIATION OF PLURIPOTENT STEM CELLS USING LAMININS LN-511, LN-521 AND LN-221

(71) Applicants: National University of Singapore, Singapore (SG); BioLamina AB, Sundyberg (SE)

(72) Inventors: Karl Tryggvason, Singapore (SG); Yan Wen Yap, Singapore (SG); Sun Yi, Sundyberg (SE); Kristian Tryggvason, Sundyberg (SE)

(73) Assignees: National University of Singapore, Singapore (SG); BioLamina AB, Sundyberg (SE)

( * ) Notice: Subject to any disclaimer, the term of this patent is extended or adjusted under 35 U.S.C. 154(b) by 482 days.

This patent is subject to a terminal disclaimer.

(21) Appl. No.: 17/226,611

(22) Filed: Apr. 9, 2021

(65) Prior Publication Data

US 2021/0301257 A1    Sep. 30, 2021

Related U.S. Application Data

(63) Continuation of application No. 14/895,669, filed as application No. PCT/IB2014/002289 on Jul. 2, 2014, now Pat. No. 11,001,807.

(60) Provisional application No. 61/842,241, filed on Jul. 2, 2013.

(51) Int. Cl.
 *C12N 5/077* (2010.01)
 *C12Q 1/6876* (2018.01)

(52) U.S. Cl.
 CPC ......... *C12N 5/0657* (2013.01); *C12Q 1/6876* (2013.01); *C12N 2501/115* (2013.01); *C12N 2501/155* (2013.01); *C12N 2501/16* (2013.01); *C12N 2501/33* (2013.01); *C12N 2501/415* (2013.01); *C12N 2501/727* (2013.01); *C12N 2501/998* (2013.01); *C12N 2506/02* (2013.01); *C12N 2533/52* (2013.01); *C12Q 2600/158* (2013.01)

(58) Field of Classification Search
 None
 See application file for complete search history.

(56) References Cited

U.S. PATENT DOCUMENTS 5,942,435 A    8/1999  Wheeler
2013/0330825 A1*  12/2013  Couture ............... C12N 5/0657
                                                    435/377

FOREIGN PATENT DOCUMENTS

WO   WO 2012/080844 A1   6/2012
WO   WO-2014011095 A1 *  1/2014 ............. A61K 35/34

OTHER PUBLICATIONS

Lian et al Nature Protocols,, 8, 162-175 (Year: 2013).*
Gonzalez et al Angew. Chem. Int. Ed. Engl. 50, 11181-11185 (Year: 2011).*
Rodin et al Nature Biotechnology, 28, 611-617 (Year: 2010).*
Nishiuchi et al Matrix Biology 25 189-197 (Year: 2006).*
Gawlik et al Skeletal Muscle 1:9, 1-13 (Year: 2011).*
Katsuhisa Matsuura et al, "Creation of mouse embryonic stem cell-derived cardiac cell sheets", Biomaterials, vol. 32, No. 30, May 12, 2011, pp. 7355-7362, Elsevier Science Publishers BV., Barking, GB.
Wei-Zhong Zhu et al: "Methods for the 1-7 Derivation and Use of Cardiomyocytes from Human Pluripotent Stem Cells" In: "Clinical Applications of Mass Spectrometry", Jan. 1, 2011, Humana Press, Totowa, NJ.
Sherwin Ting et al: "Differentiation of Human Embryonic Stem Cells to Cardiomyocytes on Microcarrier Cultures" In: "Current Protocols in Stem Cell Biology", May 1, 2012, John Wiley & Sons, Inc., Hoboken, NJ, USA.
Domogatskaya Anna et al: "Laminin-511 but not—332, -111, or -411 enables mouse embryonic stem cell self-renewal in vitro", Stem Cells, vol. 26, No. 11, Nov. 2008, pp. 2800-2809, Alphamed Press, Inc, United States.
Nobuaki Shiraki et al: "Efficient Differentiation of Embryonic Stem Cells into Hepatic Cells In Vitro Using a Feeder-Free Basement Membrane Substratum", vol. 6, No. 8, Aug. 26, 2011, p. e24228, PLOS ONE.
Aumailley M et al: "A simplified laminin nomenclature", Matrix Biology, Elsevier, NL, vol. 24, No. 5, Aug. 1, 2005, pp. 326-332.
Yap et al., "In Vivo Generation of Post-infarct Human Cardiac Muscle by Laminin-Promoted Cardiovascular Progenitors," Cell Reports, 26, 3231-3245, 2019.
Batalov et al, "Differentiation of Cardiomyocytes from Human Pluripotent Stem Cells Using Monolayer Culture," Biomarker Insight, 10(s1), 71-76, 2015.
Von Der Mark et al., "Alternative Splice Variants of a7B1 Integrin Selectively Recognize Different Laminin Isoforms," Journal of Biological Chem., 277(8), 6012-6016, 2002.
Brevini et al., "No shortcuts to pig embryonic stem cells," Embryonic Stem Cells in Domestic Animals, Theriogenology, vol. 74, 544-550, 2010.
Paris et al., "Equine embryos and embryonic stem cells: Defining reliable markers of pluripotency," Theriogenology, vol. 74, 516-524, 2010.

(Continued)

*Primary Examiner* — Anoop K Singh
(74) *Attorney, Agent, or Firm* — Lippes Mathias LLP

(57) ABSTRACT

The present disclosure describes methods of differentiating cardiomyocyte progenitor cells and mature cardiomyocyte cells from pluripotent stem cells. The methods may include differentiating pluripotent stems cells on a substrate including (i) laminin-511 or 521 and (ii) laminin 221. The mature cardiomyocyte cells produced by the method may form a human heart muscle cell line for use in regenerative cardiology.

8 Claims, 15 Drawing Sheets

(56) References Cited

OTHER PUBLICATIONS

Munoz et al., "Constraints to Progress in Embryonic Stem Cells from Domestic Species," Theriogenology, vol. 69, 1159-1164, Jan. 29, 2009.

Lian et al., "Directed cardiomyocyte differentiation from human pluripotent stem cells by modulating Wnt/B-catenin signaling under fully defined conditions," Nature Protocols, vol. 8, 162-175, 2013.

Gonzalez, R. et al, "Stepwise Chemically Induced Cardiomyocyte Specification of Human Embryonic Stem Cells," Angewandte Chemie Int. Ed. Engl. 50, 11181-11185, 2011.

Gawlik et al., "Skeletal muscle laminin and MDC1A: pathogenesis and treatment strategies," Skeletal Muscle, 1:9, 1-13, 2011.

Nishiuchi et al., "Ligand-binding specificities of laminin-binding integrins: A comprehensive survey of laminin-integrin interactions using recombinant integrins," Matrix Biology 25, 189-197, 2006.

Ting et al., "Differentiation of Human Embryonic Stem Cells to Carfiomyocytes on Microcarrier Cultures," Current Protocols in Stem Cell Biology, Supplement 21, John Wiley & Sons, Inc., 1D.7.1-1D.7.14, 2012.

Matsuura et al., "Creation of mouse embryonic stem cell-derived cardiac cell sheets," Biomaterials 32, 7355-7362, 2011.

\* cited by examiner

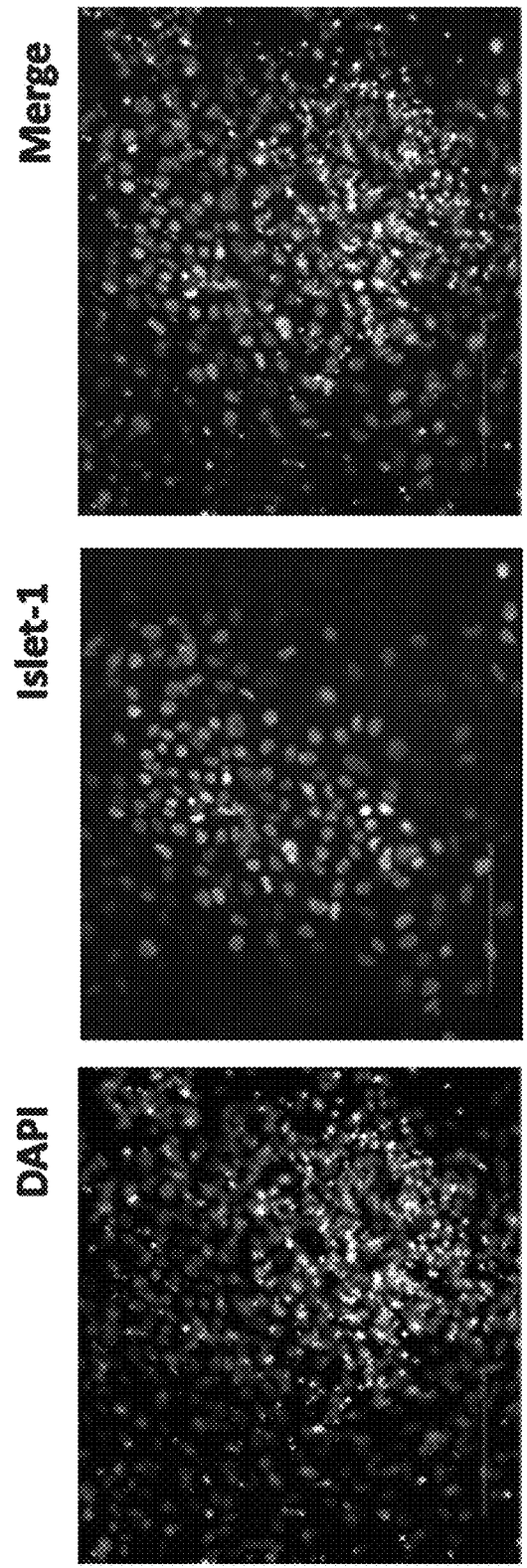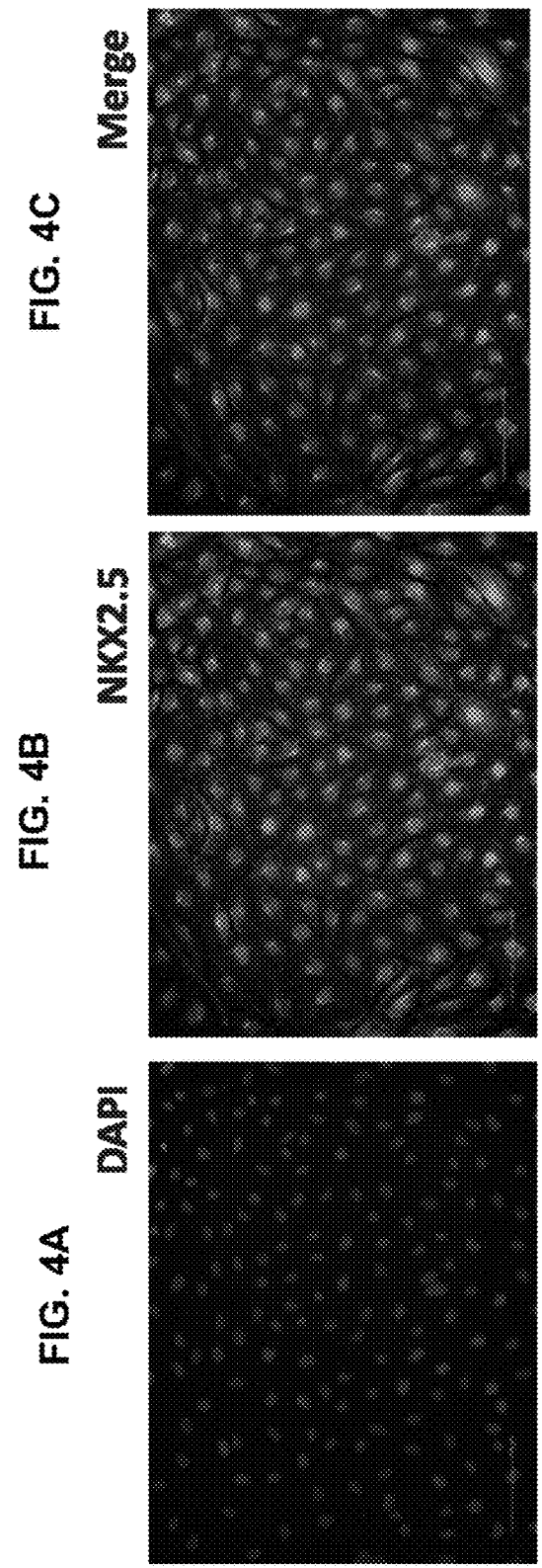
FIG. 4A  FIG. 4B  FIG. 4C
FIG. 4D  FIG. 4E  FIG. 4F

DIFFERENTIATION OF PLURIPOTENT STEM CELLS USING LAMININS LN-511, LN-521 AND LN-221

This application is a continuation of U.S. patent application Ser. No. 14/895,669, filed on Dec. 3, 2015, now U.S. Pat. No. 11,001,807, which is a 371 of PCT Application No. PCT/IB2014/002289, filed Jul. 2, 2014, which claims priority to U.S. Provisional Patent Application Ser. No. 61/842,241, filed on Jul. 2, 2013. The contents of those applications are fully incorporated by reference herein.

BACKGROUND

The present disclosure relates to methods for generating cardiomyocyte progenitors and cardiomyocytes from pluripotent stem cells using laminin substrates. It finds particular application in the differentiation of cardiomyocytes from pluripotent stem cells using (1) laminin-521 or laminin-511 and (2) laminin-221. The method allows for a controllable generation of cardiomyocyte progenitor cells and differentiated cardiomyocytes for various applications including regenerative cardiology and testing for drug effects and cardiotoxicity.

A stem cell is an undifferentiated cell from which specialized cells are subsequently derived. Examples of stem cells in the human body include pluripotent stem cells, embryonic stem cells, adult stem cells, fetal stem cells, and amniotic stem cells. Embryonic stem cells possess extensive self-renewal capacity and pluripotency with the potential to differentiate into cells of all three germ layers. Also, induced pluripotent stem (iPS) cells generated from differentiated cells with the help of specific transcription factors are also pluripotent.

Totipotency refers to a cell that has the ability to differentiate into any cell in the body, including extraembryonic tissue. Pluripotency refers to a cell that has the potential to differentiate into cells of all three germ layers. Pluripotent cells however cannot form extraembryonic tissue, as a totipotent cell can. Multipotency refers to a cell that can differentiate into cells of limited lineage. For example, a hematopoietic stem cell can differentiate into several types of blood cells, but cannot differentiate into a brain cell.

The process by which a stem cell changes into a more specialized cell is referred to as differentiation. For example, some differentiated cells include heart cardiomyocyte cells, which are derived from pluripotent human embryonic stem cells (hESCs). The process by which a specialized cell reverts back to a higher degree of potency (i.e. to an earlier developmental stage) is referred to as dedifferentiation. In particular, cells in a cell culture can lose properties they originally had, such as protein expression or shape, after undergoing the dedifferentiation process. A differentiated cardiomyocyte cell, for example, may loose its cellular phenotype, specialized characteristics, or ability to be transplanted to the heart region after the dedifferentiation process.

Cell therapy based regenerative medicine using differentiated cells holds promise as a treatment for a variety of tissue injuries. Examples of potential disease targets for cell therapy include cardiac injuries (e.g. myocardial infarction), type I diabetes (destruction of insulin producing beta cells) and Parkinson's disease (lack of dopamine producing neurons). A prerequisite for generating cells for such therapy is a possibility to differentiate the cells to specific cell types with defined reproducible protocols and obtain large quantities of human cells with stable differentiated cellular phenotypes that are suitable for transplantation to the site of injury.

There is also an urgent need for new, innovative and human-predictive cell assays within the global pharmaceutical industry since drug discovery issues, such as toxicity and lack of efficacy, are leading causes for drug failure/attrition during the pre-clinical as well as clinical stage. Currently used cell systems are not sufficient due to a number of limitations. One significant limitation is that differentiated cells often dedifferentiate in in vitro cell cultures. Moreover, many human primary cell types needed for drug discovery, like cardiomyocytes and neuronal cells, are for various reasons almost inaccessible.

BRIEF DESCRIPTION

The present disclosure relates to the development and expansion of heart progenitor cells and mature cardiomyocytes by maintaining stem cells on a combination of embryonic laminin LN-521 or LN-511, together with the most abundant and highly heart muscle specific laminin, LN-221. This new type of differentiation protocol provides completely chemically defined and animal reagent-free conditions that are a prerequisite for use of such cells for pharmaceutical development or as the direct use in human cell therapies. Disclosed herein are methods for generating cardiomyocyte progenitor cells and mature cardiomyocytes through differentiation of pluripotent stem cells on cell culture substrates including particular laminins.

In some embodiments, methods for differentiating cardiomocyte cells from a pluripotent stem cell comprise maintaining a pluripotent stem cell onto a cell culture substrate including LN-521 or LN-511, seeding the pluripotent stem cell onto a substrate including (i) LN-521 or LN-511 and (ii) LN-221, and culturing the pluripotent stem cells in a basal medium to form cardiomyocyte progenitor cells. The basal medium does not contain any inhibitors of apoptosis.

The methods may include differentiating the cardiomyocyte progenitor cells on the substrate to form mature cardiomyocyte cells.

The methods may also include culturing the pluripotent stem cells in the presence of a GSK-3 inhibitor to stimulate Wnt signaling.

The methods may include culturing the pluripotent stem cells in the basal medium devoid of inhibitors.

The methods may also include transforming the mature cardiomyocyte cells into contracting (beating) aggregated muscle fibers.

The methods may include clustering the pluripotent stem cells in the presence of Wnt inhibitor to suppress Wnt signaling.

The methods may also include a cell culture coating where at least one of LN-521, LN-511, and LN-221 is an effective recombinant laminin.

The methods may include a cell culture substrate and combination cell culture substrate without any differentiation inhibitors, feeder cells, differentiation inductors, or apoptosis inhibitors.

The methods may further include applying a cell culture medium to the pluripotent stem cells.

The methods may also include cardiomyocyte progenitor cells which express Islet-1, NKX2.5, as well as other transcription factors.

The methods may further include the aggregated muscle fibers and beating cell sheets expressing Troponin T, myosin light chain for ventricular cells (MLC2v), and myosin sarcomere filament (MF-20) biomarkers.

In other embodiments, a progenitor cardiomyocyte cell is formed from the differentiation of pluripotent stem cells on a combination cell culture substrate including at least one of (i) LN-511 and LN-521, and (ii) LN-221.

The progenitor cardiomyocyte cell may express Islet-1 and NKX2.5 transcription factor.

In some embodiments, a mature cardiomyocyte cell is formed from the differentiation of pluripotent stem cells on a combination cell culture substrate including at least one of LN-511 and LN-521, and LN-221.

The mature cardiomyocyte cell may form a muscle fiber or beating cell sheet expressing Troponin T, myosin light chain for ventricular cells (MLC2v), and myosin sarcomere filament (MF-20) biomarkers.

The muscle fiber may have a beating, striated phenotype.

In other embodiments, methods for forming a heart muscle fiber with a beating striated phenotype may include differentiating pluripotent stem cells on a substrate including (i) LN-521 or LN-511 and (ii) LN-221, to form mature cardiomyocyte cells, and transforming the mature cardiomyocyte cells into a cardiomyocyte-like heart muscle fiber having a beating, striated phenotype.

In some methods, the pluripotent stem cell is a human embryonic stem cell (hESC). In other embodiments, a heart muscle fiber having a beating, striated phenotype is generated by the differentiation of pluripotent stem cells on a cell culture combination substrate including (i) LN-521 or LN-511 and (ii) LN-221.

The heart muscle fiber may be generated by the differentiation of a human embryonic stem cell (hESC).

Also disclosed herein are the cells and muscle fibers created using the methods described herein.

BRIEF DESCRIPTION OF THE DRAWINGS

The following is a brief description of the drawings, which are presented for the purposes of illustrating the exemplary embodiments disclosed herein and not for the purposes of limiting the same.

FIG. 3A includes a high level summary of method steps according to one embodiment of differentiating hES cells to beating cardiomyocytes including an indication of which pluripotency markers should be expressed on different days. FIG. 3B includes a day-by-day illustration of steps which correspond with a method of differentiating pluripotent stem cells to beating cardiomyocytes. FIG. 3C includes a detailed illustration of method steps according to another embodiment of differentiating cardiomyocytes.

FIGS. 4A-4F include photomicrographs and flow cytometry analysis of cardiac progenitor cells. FIG. 4A details the expression of DAPI for nuclei. FIG. 4B details Islet-1 transcription factor (red). FIG. 4C details a merger of DAPI and Islet-1 transcription factor expression in cardiomyocyte progenitor cells derived from hESCs. FIG. 4D details the expression of DAPI for nuclei. FIG. 4E details NKX2.5 transcription factor and in FIG. 4F a merger of DAPI and NKX2.5 transcription factor expression in cardiomyocyte progenitor cells derived from hESCs. FIGS. 4A-4F show that Islet-1 and NKX2.5 expression is located in the nucleus of the cells, which strongly suggests the presence of cardiomyocyte progenitors.

FIG. 5A is the analysis by phenotype, where defined colonies were formed when the cells were maintained on LN-521. FIG. 5B is a flow cytometry analysis. The NKX2.5 measurements are labeled with triangles, the Islet-1 measurements are labeled with diamonds, and the isotype control is labeled with circles. In FIG. 5C, progenitors analyzed with Islet-1 and NKX2-5 antibody measured >99% positivity for both markers. The NKX2.5 measurements are labeled with circles, the Islet-1 measurements are labeled with triangles, and the isotype control is labeled with diamonds. In both graphs, the y-axis is the number of cells expressing a certain level of APC-A, which is indicated on the x-axis.

FIG. 8A shows the analysis for cardiac troponin T (cTNT). FIG. 8B shows the analysis for cardiac myosine sacromeric protein (MF20). In these two graphs, the y-axis is the number of cells expressing a certain level of the protein (indicated on the x-axis). The line indicated by circles is for the protein, while the line indicated by diamonds is the isotype control. In FIG. 8A, 82.2% of cells are positive for cTNT, and 17.8% of cells are negative for cTNT. In FIG. 8B, 86.8% of cells are positive for MF20. Both analyses were >80% positive.

FIG. 8C shows electrophysiology analysis by patch clamp recording revealed action potential from all 3 subtypes of cardiomyocytes in the heart namely ventricular-like, nodal-like and atrial-like cells.

FIG. 9A shows decreased expression of pluripotent genes to negligible levels after 30 days. FIG. 9B shows temporal expression of progenitor specific genes indicative of mesodermal lineage specification and cardiomyocyte specialization. FIG. 9C shows increased expression of cardiomyocyte specific genes after day 9.

DETAILED DESCRIPTION

Figure 1:
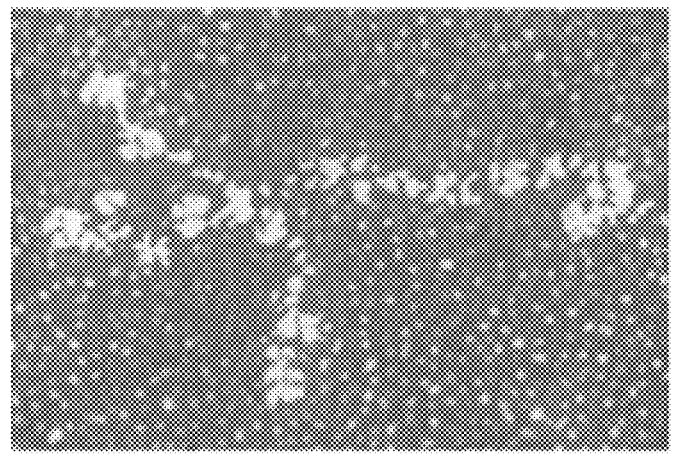
FIG. 1 is a rotary shadowing electron microscopy picture of a single recombinant laminin molecule containing α, β and γ chains. It reveals three short arms with small globular domains and one long arm with a large globular domain at the terminal end.

A more complete understanding of the compositions and methods disclosed herein can be obtained by reference to the accompanying drawings. These figures are merely schematic representations based on convenience and the ease of demonstrating the present disclosure, and are, therefore, not intended to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

All publications, patents, and patent applications discussed herein are hereby incorporated by reference in their entirety.

The methods of the present disclosure are related to maintaining the phenotype of differentiated cells. The term "phenotype" here refers to the cell's observable characteristics and properties. These include such things as the cell's morphology, biochemical or physiological properties, etc. It is desirable to maintain the cell's phenotype, particularly when the cells are going to be used for cell therapy or pharmacological or toxicologic testings.

Due to their unique properties to renew indefinitely and their capacity to form all somatic derivatives of the human body, human pluripotent stem cells (hPSC) have a huge potential to be used in regenerative medicine. HiPS cells may also find applications in cell therapy, but also as model systems for studying aspects of human genetic diseases if the iPS cells are generated from individuals with a genetic disease. Another interesting perspective of hPSCs is their use in drug discovery in vitro where they generate wide interest for pharmaceutical research, spanning from early target studies to drug metabolism and pharmacokinetics studies or safety assessment. Cell-based in vitro assays with high human relevance are urgently needed for pre-clinical activities.

Currently used human cell systems are hampered by the fact that primary cells or available cell lines either rapidly lose specific functions, or they already lack these properties. Furthermore, many human primary cell types, like cardiomyocytes, are practically inaccessible for cell therapy of tissue damage like cardiac infarction, type I diabetes and Parkinson's disease, or drug and toxicity testing. hPSCs differentiated into functional progenitor of fully differentiated cells can provide a virtually unlimited supply of homogeneous human cell material needed in pharmaceutical research and development, which greatly facilitates broader screening activities like comparative studies or high-throughput compound testing. Moreover, genetic diversity and human variability can be easily addressed since specialized cells can be derived from multiple hESC-lines.

Full exploitation of the potential of hPSCs in these areas has for long been limited by several major technical hurdles: (1) Culturing of hPSC without loss of pluripotency has been problematic; (2) Culturing of hPSCs was until recently impossible without the support of feeder cells or various animal supplements; (3) Genetic stability without the introduction of chromosomal changes has so far required "manual passaging" of hPSC colonies, severely limiting the scalability of culture; (4) Derivation of specific differentiated cell lineages relevant for therapeutic treatments, disease modeling or pharmaceutical research has been extremely inefficient, and; (5) cells differentiated from hPSC-derivatives are most often immature and do not adequately correspond to the differentiated cells in the recipient tissue or organ after transplantation. These technical hurdles may be addressed by using particular biologically relevant laminin substrates and/or other taking other steps during the generation of differentiated cells.

Differentiated cells require two things to survive and reproduce: (1) a substrate or coating that provides a structural support and outside-in signals to the cell; and (2) a cell culture medium to provide nutrition, growth factors and hormones to the cell. The substrate or coating (1) is generally placed on, for example, the surface of a petri dish, microtiter plate or some other container. It is particularly contemplated that the cell culture substrate on which the differentiated cell is plated comprises a laminin.

Laminins are a large family of heterotrimeric glycoproteins that reside primarily in the basal lamina immediately adjacent to the cell membrane. On the one hand, they function via binding interactions with neighboring cell receptors on the one side, and by binding to other laminin molecules or other matrix proteins such as other laminins, collagens, nidogens or proteoglycans. The laminin molecules have several subdomains in different regions of the molecule which bind cell receptors and other molecules in the extracellular matrix. The laminin molecules are important signaling molecules that can strongly influence cellular behavior and function via binding to signaling receptors. Laminins are important in both maintaining cell/tissue phenotype, as well as in promoting cell growth, differentiation, adhesion and migration in tissue repair and development.

Laminins are large, multi-domain proteins, with a common structural organization. The laminin molecule integrates various matrix and cell interactive functions into one molecule.

A laminin protein molecule comprises one α-chain subunit, one β-chain subunit, and one γ-chain subunit, all joined together in a trimer through a coiled-coil domain (1). FIG. 1 depicts the resulting structure of the laminin molecule. The twelve known laminin subunit chains can form at least 16 trimeric laminin types in native tissues. Within the trimeric laminin structures are identifiable domains that possess binding activity towards other laminin and basal lamina molecules, as well as membrane-bound receptors.

Figure 2A:
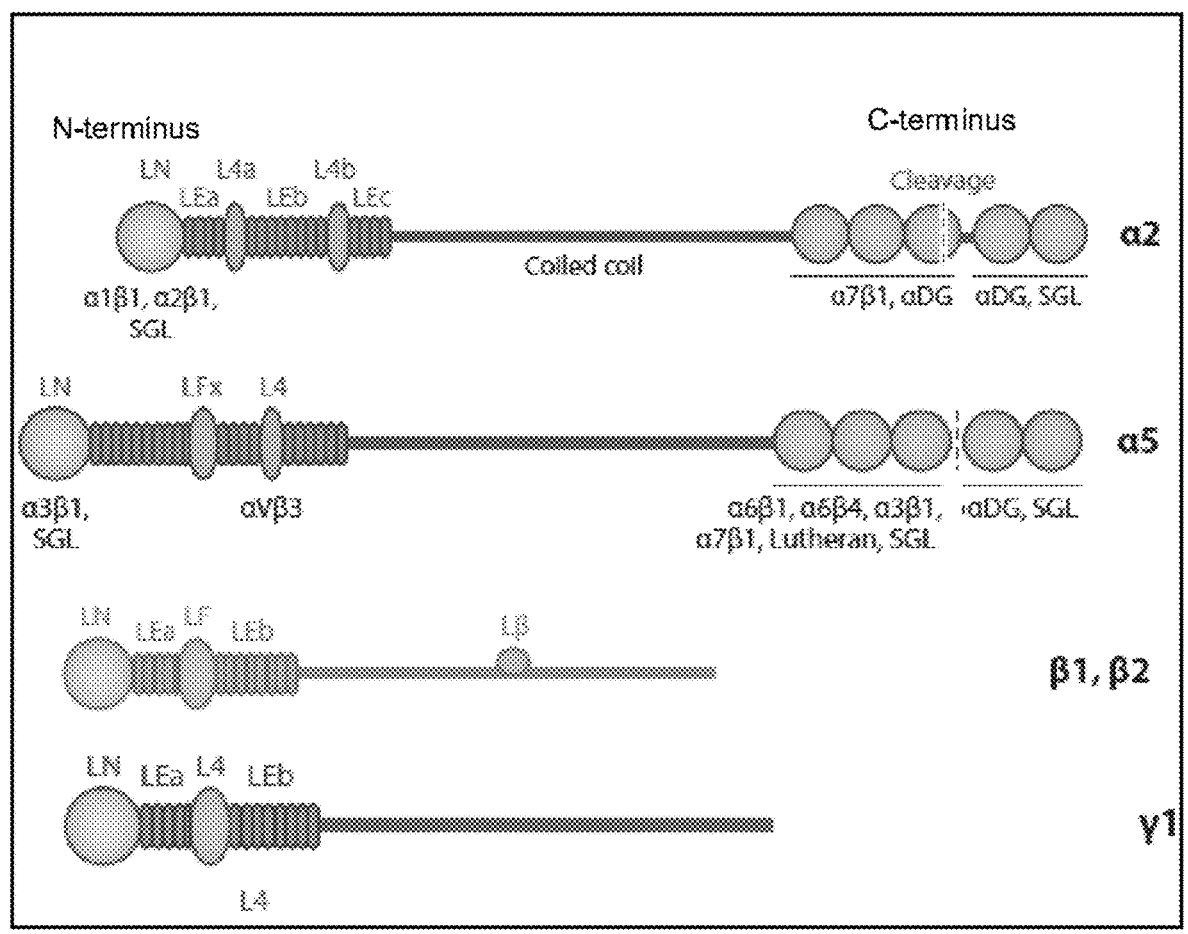
FIG. 2A is a drawing of the structural motifs of laminin α2, α5, β1, β2 and γ1 chains. Each laminin chain contains tandem arrays of globular and rod-like domains.

FIG. 2A shows the three laminin chain subunits (alpha-5 chain, alpha-2 chain, beta-1 chain, beta-2 chain and gamma-1, separately. For example, domains VI, IVb, and IVa form globular structures, and domains V, IIIb, and IIIa (which contain cysteine-rich EGF-like elements) form rod-like structures. Domains I and II of the three chains participate in the formation of a triple-stranded coiled-coil structure (the long arm).

With continuing reference to FIG. 2A, each laminin chain contains tandem arrays of globular and rod-like domains. The α chains have five globular subdomains or motifs (LG 1-5) at the C-terminus. In α2 and α5, LG 4-5 are believed to be normally cleaved off extracellularly, while all LG motifs are probably intact in functional α1 and α2 chains. The LG domain is the main cell receptor binding region, but other domains may also interact with cellular receptors. The LG 1-3 domains bind to integrins, while LG 4 and LG 5 contain binding sites for dystroglycan (DG) and sulfated glycolipids (SGL). A small globular motif (Lβ) in the coiled-coil domain of the β chains binds to agrin. The N-terminal end of all the chains contains variable amount of EGF-like repeats in short rod-like domains (LEa-c), as well as 1-3 globular domains (L-N, L4, L4a, L4b, LFx).

There exist five different alpha chains, four beta chains and three gamma chains that in human tissues have been found in at least fifteen different combinations (1). These molecules (isoforms) were previously named as laminin-1, laminin-2, etc. according to their order of discovery, but currently they are named according to their chain composition, e.g. laminin-111 (laminin-1) that contains alpha-1, beta-1 and gamma-1 chains. Four structurally defined family groups of laminins have been identified. The first group of five identified laminin molecules all share the β1 and γ1 chains, and vary by their α-chain composition (α1 to α5 chain). The second group of five identified laminin molecules, including laminin-521, all share the β2 and γ1 chain, and again vary by their α-chain composition. The third group of identified laminin molecules has one identified member, laminin-332, with a chain composition of α3β3γ2. The fourth group of identified laminin molecules has one identified member, laminin-213, with the newly identified γ3 chain (α2β1γ3).

Generally, the cell culture substrate may contain any effective laminin, wherein the effectiveness is determined by whether differentiated cells can survive upon the substrate. It is specifically contemplated that the substrate contains either one or more particular laminins, though other ingredients may also be present in the substrate. In one embodiment, the laminin is laminin-521 (LN-521) or laminin-511 (LN-511). In other specific embodiments, the laminin is (i) LN-521 or LN-511 in combination with (ii) LN-221.

The term "laminin-521" refers to the protein formed by joining α5, 2 and γ1 chains together. The term "laminin-511" refers to the protein formed by joining α5, 31 and γ1 chains together. The term "laminin-221" refers to the protein formed by joining α2, β2 and γ1 chains together. These terms should be construed as encompassing both the recombinant laminin and heterotrimeric laminin from naturally occurring sources. The term "recombinant" indicates that the protein is artificially produced using expression plasmids in cells that do not normally express such proteins.

The laminin can be an intact protein or a protein fragment. The term "intact" refers to the protein being composed of all of the domains of the α-chain, β-chain, and γ-chain, with the three chains being joined together to form the heterotrimeric structure. The protein is not broken down into separate chains, fragments, or functional domains. The term "chain" refers to the entirety of the alpha, beta, or gamma chain of the laminin protein. The term "fragment" refers to any protein fragment which contains one, two, or three functional domains that possesses binding activity to another molecule or receptor. However, a chain should not be considered a fragment because each chain possesses more than three such domains. Similarly, an intact laminin protein should not be considered a fragment. Examples of functional domains include Domains I, II, III, IV, V, VI, and the G domain. Further information of these domains is found in Domogatskaya, A., Rodin, S., and Tryggvason, K. 2012. Functional diversity of laminins. *Annu Rev Cell Dev Biol* 28:523-553, which is incorporated by reference.

The laminins can theoretically form over 50 different combinations, but at least 16 have been identified in mammals. The laminins are important for cell differentiation in the embryo, are major cell attachment molecules, are important for cell migration and defined and xeno-free and has been shown to provide a biological relevant in-vitro environment.

Figure 2B:
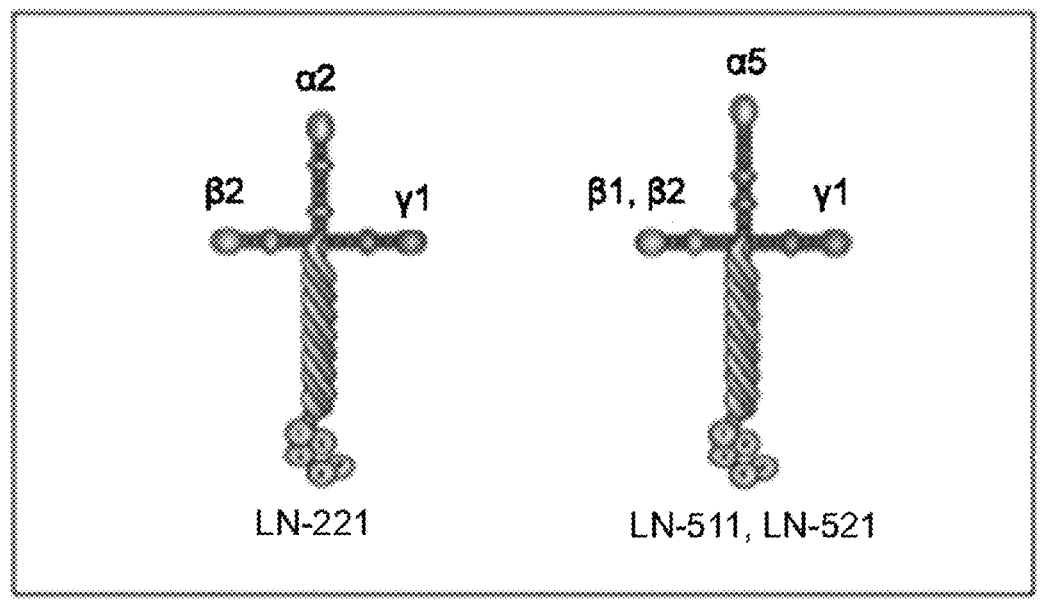
FIG. 2B is a drawing of laminin α, β and γ chains assembling to form a coiled-coil in at least 16 combinations. Here, the trimeric laminins LN-221 and LN-511 and LN-521 are illustrated.

With reference to FIG. 2B, the laminin and α, β and γ chains assemble to form a coiled-coil in at least 16 combinations. Here, the trimeric laminins LN-221 and LN-521 are illustrated. Further information on LN-211, LN-511, and LN-521 is found in Aumailley, M., Bruckner-Tuderman, L., Carter, W. G., Deutzmann, R., Edgar, D., Ekblom, P., Engel, J., Engvall, E., Hohenester, E., Jones, J. C., et al. 2005. A simplified laminin nomenclature. *Matrix Biol* 24:326-332, which is incorporated by reference.

Different laminins are important for different cell types, both for their formation and phenotype maintenance. For example, LN-521 and LN-511 support efficient, long-term maintenance and propagation of hPSCs and hiPSCs without a risk of spontaneous differentiation or genetic changes. Further information on LN-521 and LN-511 is found in Rodin, S., Domogatskaya, A., Strom, S., Hansson, E. M., Chien, K. R., Inzunza, J., Hovatta, O., and Tryggvason, K. 2010. Long-term self-renewal of human pluripotent stem cells on human recombinant laminin-511. *Nat Biotechnol* 28:611-615, and Rodin, S. et al in *Nat Commun*, Jan. 27, 2014, which are incorporated herein by reference. LN-521 together with E-cadherin as a matrix facilitate clonal derivation of hES cells from an in vitro fertilized embryo without a need to destroy the embryo. See Rodin, S. et al. *Nat Commun*, Jan. 27, 2014.

LN-211 and LN-221 are highly specific for cardiac and skeletal muscle fibers (cells), and they also have important roles in the nerve system. However, LN-221 is the most abundant laminin isoform in human cardiac muscle, being about 3 times more abundant than LN-211 based on global transcriptome analysis from the heart ventricle. The other most common laminins present in heart muscle are LN-511 and LN-521.

Heart muscle cell (cardiomyocyte) progenitors and mature cardiomyocytes, are of critical importance for the development of cell therapy of heart muscle injury. Although pluripotent stem cells can be differentiated towards cardiomyocytes by culturing them on extracellular matrix substrata such as murine Matrigel™, or on feeder cells such as human or mouse fibroblasts, 3 dimensional embryoid body (EB) differentiation or inductive co-culture with END2 cells in the presence of differentiation conditions, these methods are not chemically defined and their results vary from one experiment to another. There is a lack of reproducibility, there is a need for inclusion of serum, heterogeneous EB sizes and/or the utilization of a complex matrix Matrigel™ that is a tumor extract containing several basement membrane proteins (e.g. type IV collagen, perlecan, laminin) as well as growth factors and intracellular proteins. Additionally, the laminin present in Matrigel is LN-111, which hardly exists in normal heart muscle. Matrigel™ is the most used cell culture coating for the maintenance of pluripotent stem cells and also the preferred substrate for cell differentiation where it is used for the re-plating of EB and monolayer differentiation. Unfortunately, Matrigel™ is isolated from a basement membrane-like matrix produced by whole mouse tumor (EHS sarcoma) tissue and, thus, it is xenogenic, affected by lot-to-lot variations and contains an extensive amount of undefined components. Moreover, cells cultured on Matrigel™ also have the possibilities to acquire non-human N-glycolylneuraminic acid (Neu5Gc) immunogen which renders them unsuitable for clinical applications.

A study by Lian et al. demonstrated that pluripotent stem cells are able to differentiate using small molecules that modulate Wnt signaling pathway in a monolayer using Matrigel™ and a commercial plate called Synthemax using mTeSR1 media with ROCK inhibitor. The exact component of Synthemax is proprietary to Corning®, however it is based on a study by Melkoumian et al. Further information on the Melkoumian study is found in Melkoumian, Z., Weber, J. L., Weber, D. M., Fadeev, A. G., Zhou, Y., Dolley-Sonneville, P., Yang, J., Qiu, L., Priest, C. A., Shogbon, C., et al. 2010. Synthetic peptide-acrylate surfaces for long-term self-renewal and cardiomyocyte differentiation of human embryonic stem cells. *Nat Biotechnol* 28:606-610, which is incorporated by reference. He reported that the synthetic RGD peptide sequence of vitronectin protein is sufficient to maintain pluripotent stem cells. However, this surface is not a biologically relevant substrate for any cells in the body. Moreover the medium used (mTeSR1) contains bovine serum albumin (BSA) and high concentration of basic FGF growth factor (100 ng/ml). On top of these, he seeded single cells that require additional ROCK inhibitor to diminish dissociated-induced apoptosis. The actual mechanism on how this inhibitor functions to promote single cells survival is still unknown. Therefore, the existence of differentiation protocols providing a completely chemically defined, controllable and xeno-free environment are desired.

The neonatal mammalian heart is capable of significant regeneration of the injured heart muscle for only about a week after birth. After that, cell cycle arrest occurs by unknown mechanisms and that hinders proliferation of cardiac cells and subsequent tissue repair. Recent progress in stem cell research and design of novel differentiation protocols has opened up for possibilities for new cell therapy approaches for treatment of cardiac muscle injury. Several types of cells have been explored for cell therapy purposes, but currently the most attractive sources include (i) cardiomyocyte progenitors or cardiomyocyte-like cells derived from either hESCs or induced (reprogrammed) pluripotent stem cells (iPSC), (ii) cardiomyocytes reprogrammed directly from fibroblasts, or (iii) cardiomyocyte progenitors isolated and expanded from embryonic or adult heart muscle tissue. The reprogrammed cell lines derived from human fibroblasts have been generated by administration of vectors containing cDNAs for various transcription factors, which can pose a problem as they involve changes in the genome. One concern is that such cells can become tumorigenic and therefore they may not be suitable for cell therapy of human disease. Therefore, it would be desirable to be able to derive cardiac progenitors or mature cardiomyocytes from pluripotent embryonic or mesenchymal stem cells or also from progenitor cells from the adult cardiac muscle tissue.

In one embodiment, a method for differentiating a human cardiac progenitor cell or mature human cardiomocyte cell from pluripotent stem cells includes maintaining hESCs on embryonic laminins LN-521 or LN-511 in the presence of laminins present in the basement membrane surrounding the muscle fiber cells, LN-211 and LN-221. Suitable laminins include specific laminin isoforms, e.g. LN-511, LN-521, LN-211 and LN-221, provided by BioLamina, AB, in Sweden.

Figure 3A:
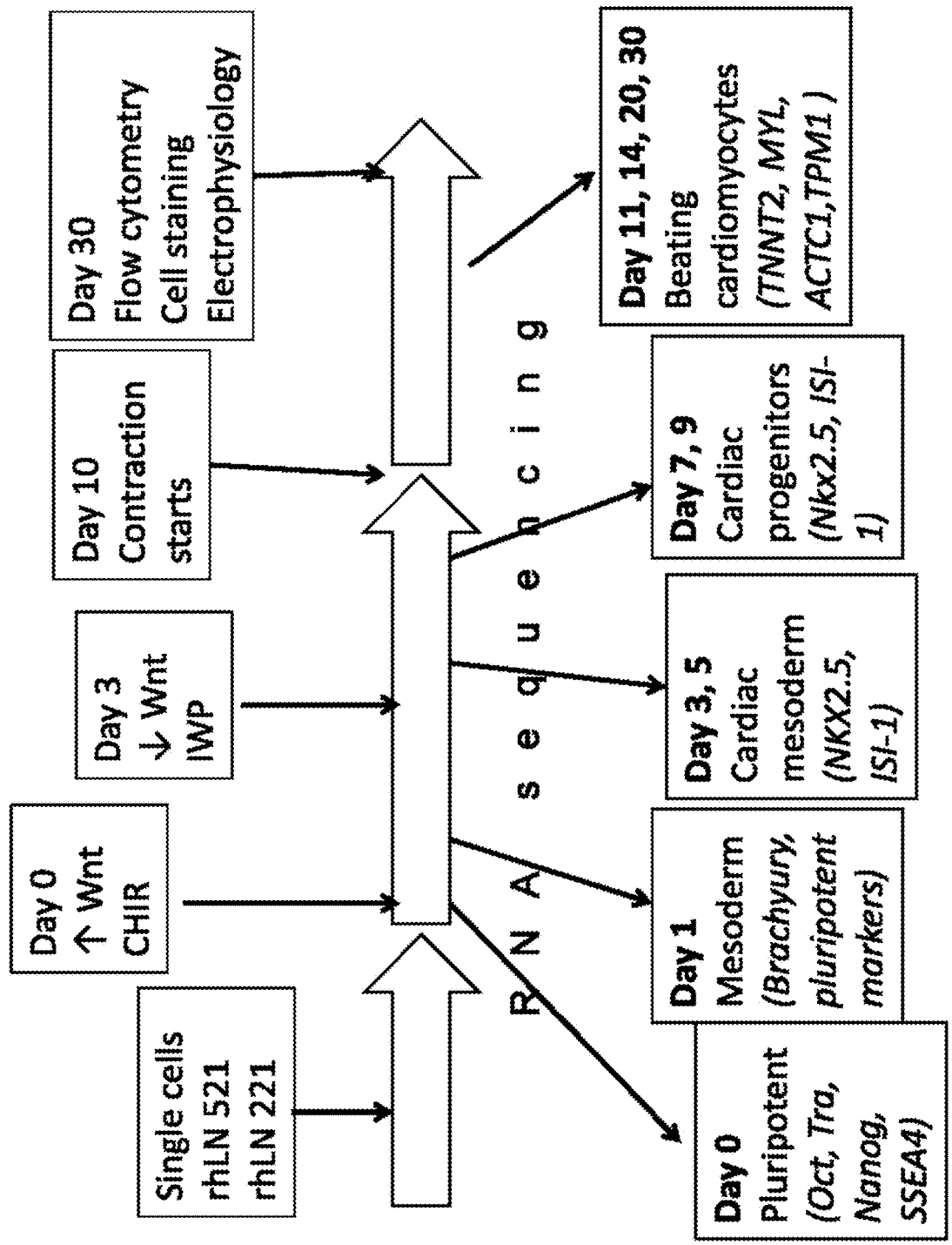
FIGS. 3A-3C include flow diagrams illustrating methods of differentiating cardiomyocytes from pluripotent stem cells.

With reference to FIG. 3A, a high level summary of method steps according to one embodiment of differentiating hES cells to beating cardiomyocytes is described. The term "CHIR" refers to a glycogen synthase kinase 3 (GSK3) inhibitor which mimics Wnt signaling preadipocytes. The term "IWP" refers to a Wnt Inhibitor which serves as an antagonist of the Wnt/I-cantenin pathway. The term "Wnt" represents Wnt proteins, which are highly conserved secreting molecules that regulate cell-to-cell interactions during embryogenesis. The acynom "rhLN" stands for recombinant human laminin.

Figure 3B:
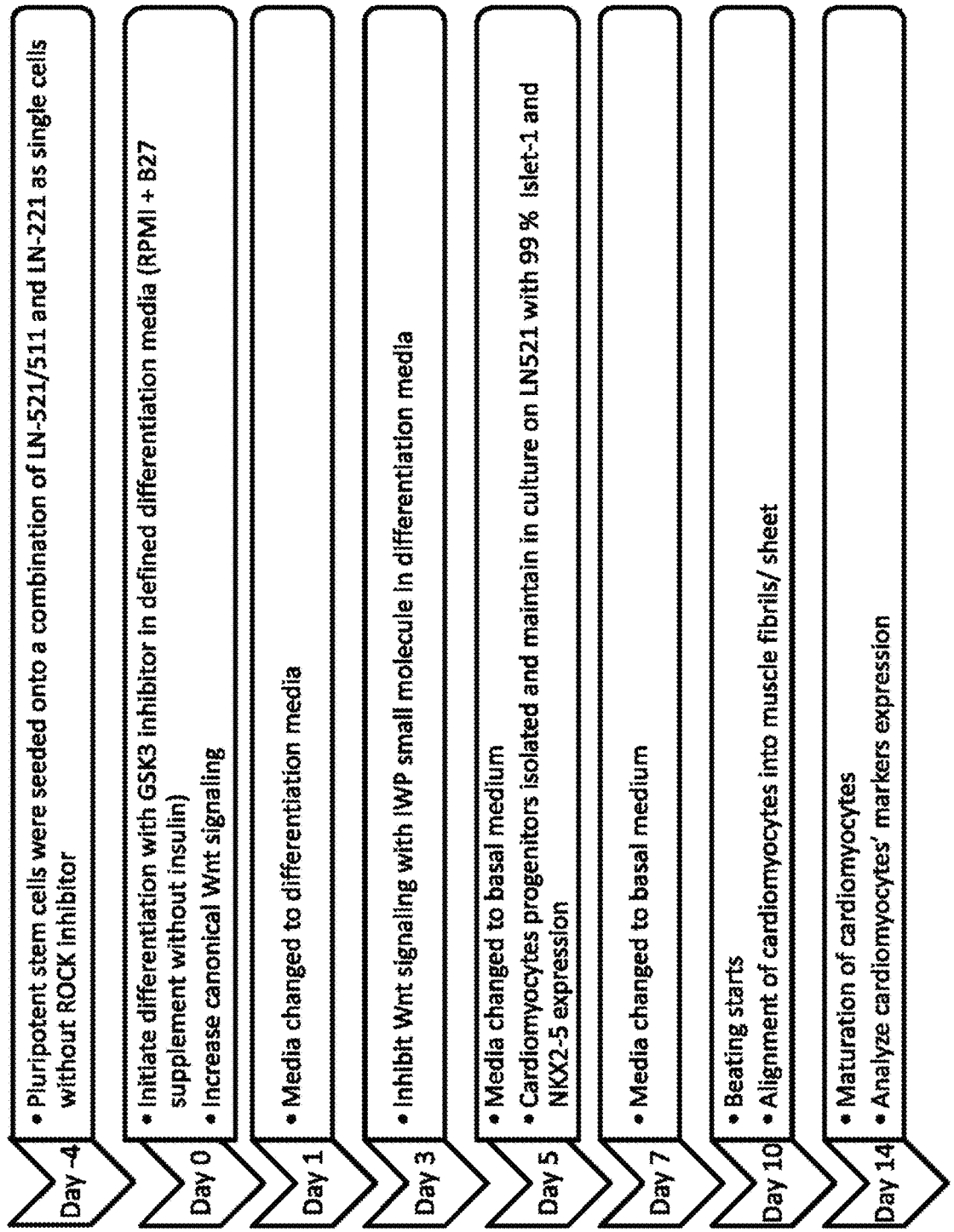

With reference to FIG. 3B, a day-by-day illustration of steps corresponding with a method of differentiating pluripotent stem cells to beating cardiomyocytes is described.

Figure 3C:
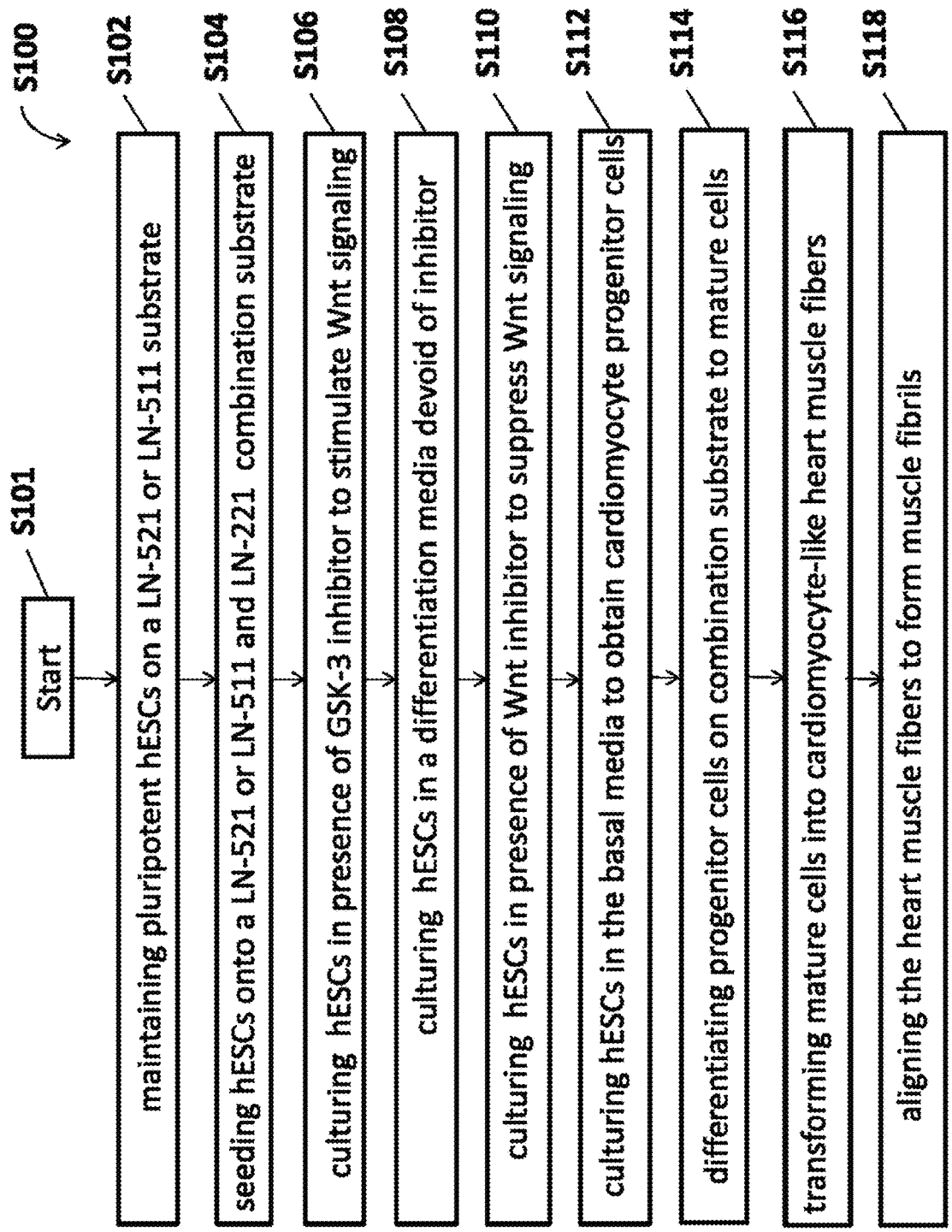

With reference to FIG. 3C, a method S100 for differentiating cardiomyocytes from pluripotent stem cells using laminin substrates according to another embodiment starts at S101.

At S102, pluripotent cells are maintained on laminin-521 (LN-521) or laminin-511 (LN-511) combined with LN-221.

At S104, the pluripotent cells are seeded onto a combination substrate including LN-521 or LN-511 and LN-221 and maintained for five days.

At S106, the pluripotent cells are cultured for one day in the presence of a differentiation medium containing a GSK-3 inhibitor to inhibit β-catenin phosphorylation, which in turn stimulates canonical Wnt signaling. Suitable GSK-3 inhibitors include CHIR 99021 from Stemgent of Cambridge, MA, and other similar inhibitors as known by one having ordinary skill in the art.

At S108, the pluripotent cells are cultured in a differentiation medium devoid of inhibitor for two days.

At S110, pluripotent cells are cultured for two days in a differentiation medium containing a Wnt inhibitor to suppress Wnt signaling.

At S112, the cells are cultured for 2 days in the basal medium where they form cardiomyocyte progenitor cells. These hESCs may express Islet-1 and NXK2.5 transcription factors, which are biomarkers for cardiomyocyte progenitor cells. Expression of the Islet-1 transcription factor is illustrated in the photomicrograph of FIGS. 4A-C. With reference to FIG. 4A, a photomicrograph of Islet-1 transcription factor expression shows cardiomyocyte progenitors derived from hESCs. Cells were immunostained in FIG. 4A with DAPI for nuclei, FIG. 4B and FIG. 4E for Islet-1, NKX2-5 and FIG. 4C, FIG. 4F showing the merged results. Results show that Islet-1 and NKX2-5 are located in the nucleus of the cells, which strongly demonstrates the presence of cardiac progenitor cells.

Figure 5A:
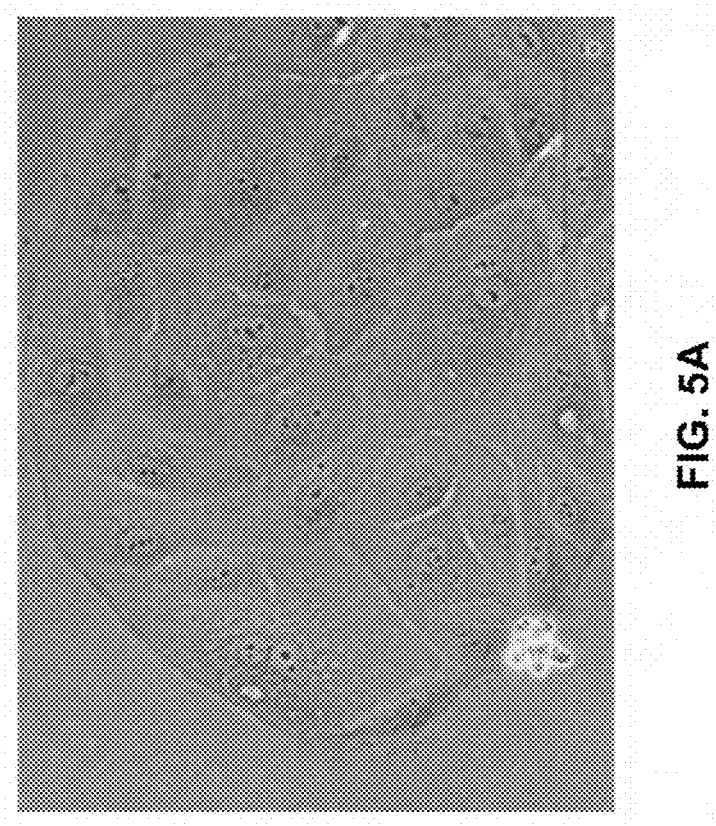
FIGS. 5A-5C include an analysis of cardiac progenitors. The cells were analyzed with Islet-1 and NKX2.5 antibodies.
Figure 5C:
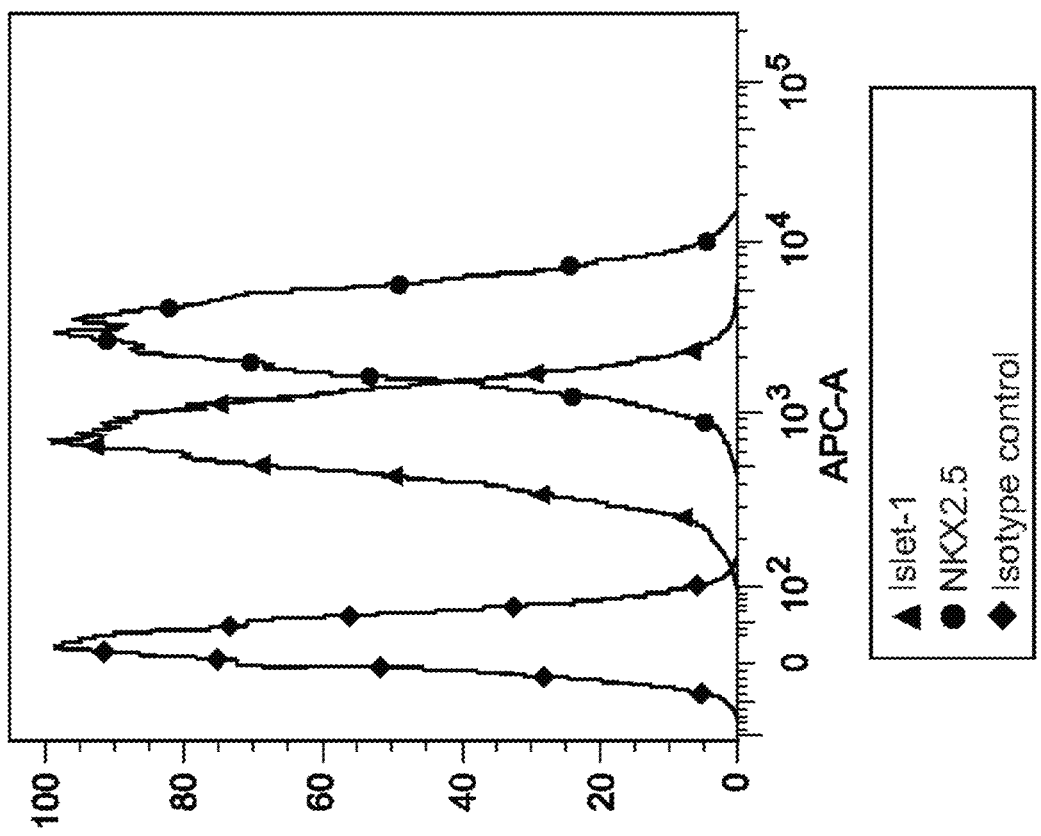

With reference to FIG. 5C, flow cytometry analysis show 99% cells are expressing Islet-1 and NKX2-5 cardiomyocytes biomarkers.

Referring back to FIG. 3C, at S114, the progenitor cells are further differentiated on the combination substrate to generate mature cardiomyocyte cells.

Figure 6A:
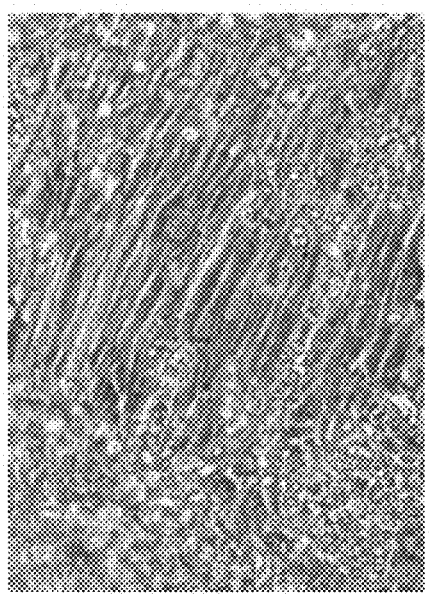
FIG. 6A and FIG. 6B are photomicrographs of cardiomyocyte like human heart muscle fibers aligned with each other length-wise into muscle fibrils.
Figure 6B:
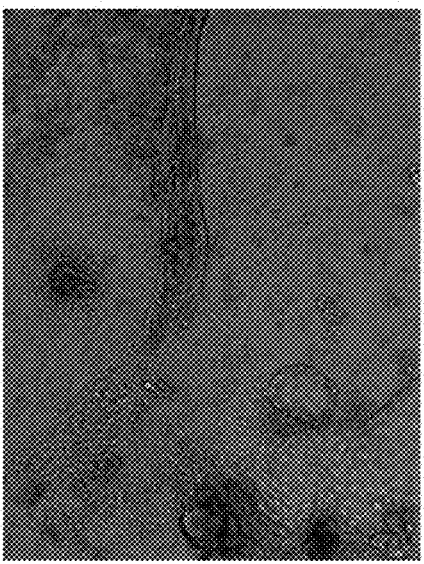
Figure 6C:
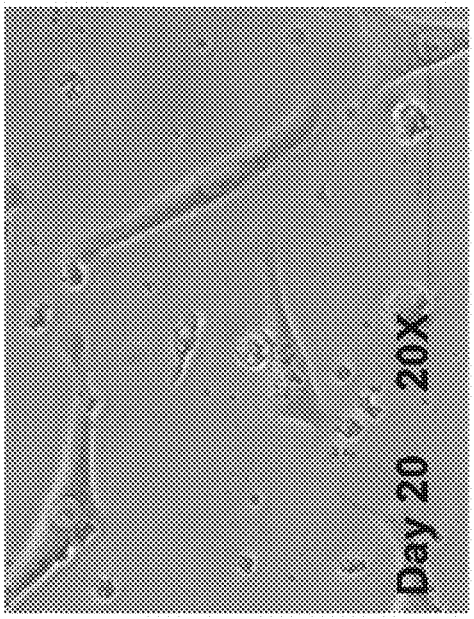
FIG. 6C is an image of single cardiomyocytes having rectangular morphology.

At S116, mature cardiomyocyte cells are transformed into cardiomyocyte like human heart muscle fibers which may be aligned pairwise into muscle fibrils, maintaining the beating, striated phenotype. The muscle fibrils are illustrated in FIG. 6A. With reference to FIG. 6C, single cardiomyocytes have a rectangular phenotype, which are the typical morphology for cardiomyocytes in the body.

Figure 5B:
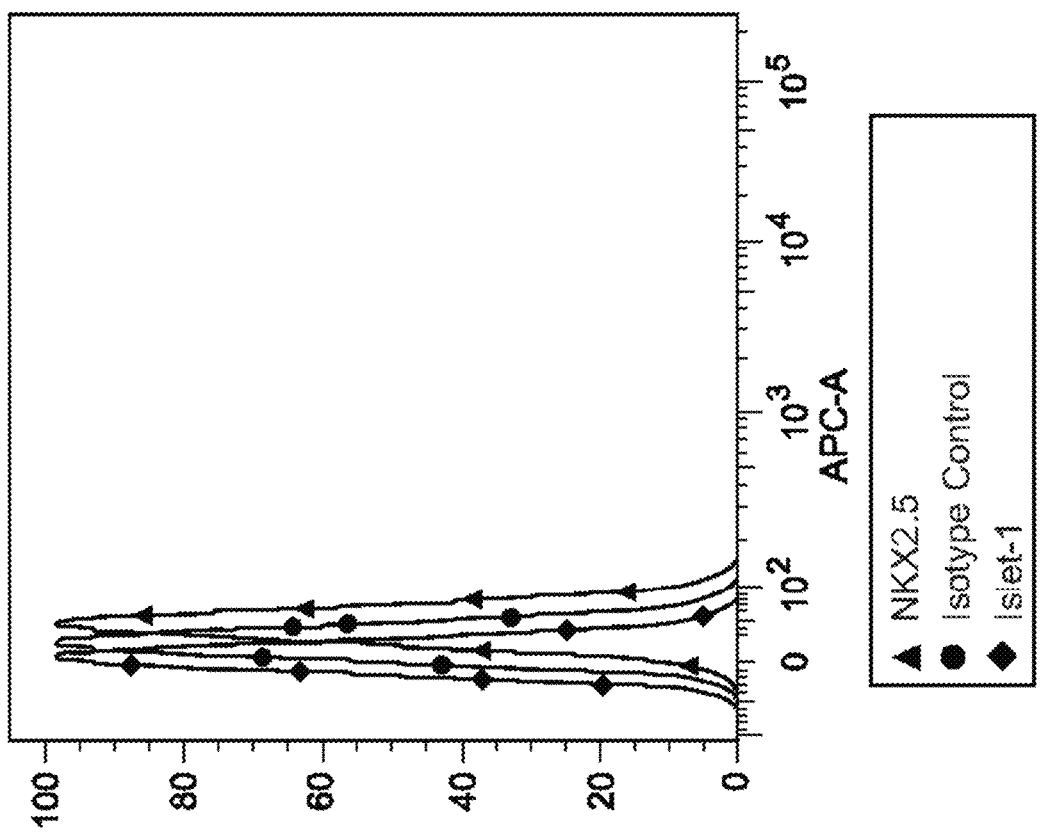
Figure 7A:
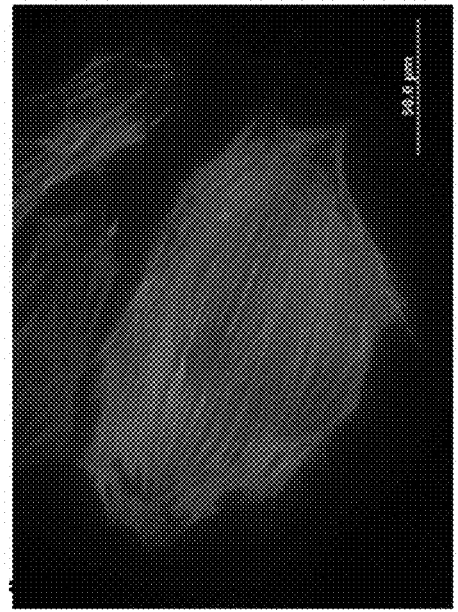
FIGS. 7A-7D include photomicrographs showing the expression of FIG. 7A cardiac troponin T (cTNT) (green), FIG. 7B cardiac troponin I (cTNI) (green), FIG. 7C myosin light chain for ventricular cells (MLC2v) (green), and FIG. 7D alpha-actinin (α-actinin) (green) biomarkers in the cardiomyocyte of FIG. 6B. Aligned sarcomere organization was observed from these staining. Nuclei were stained with DAPI.
Figure 7B:
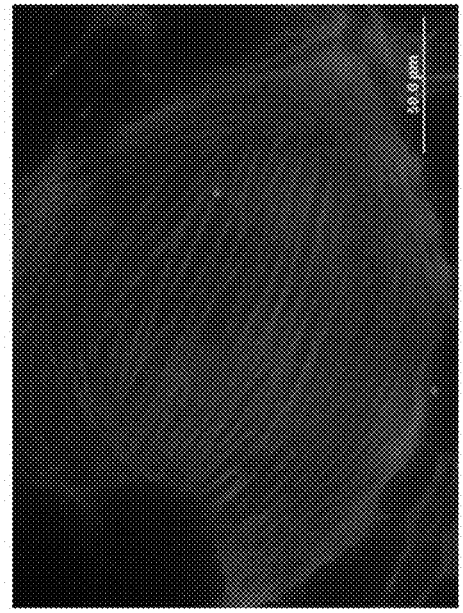
Figure 7C:
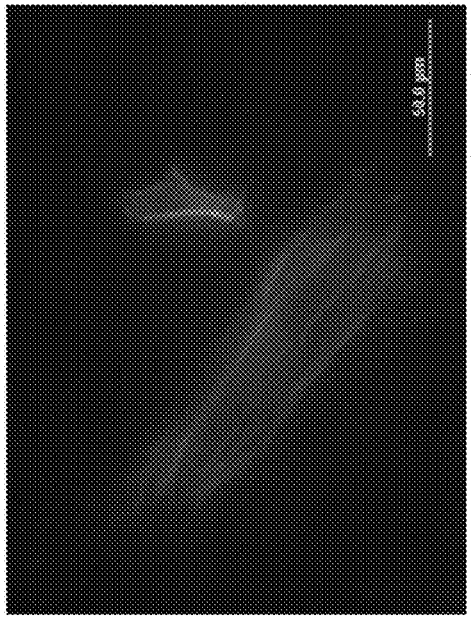
Figure 7D:
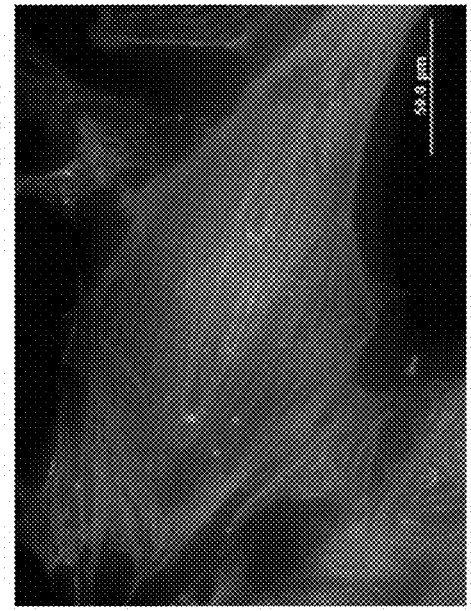

With reference to FIG. 7, a photomicrograph shows the expression of FIG. 7A cardiac troponin T (cTNT) (green), FIG. 7B cardiac troponin I (cTNI) (green), FIG. 7C myosin light chain for ventricular cells (MLC2v) (green) and FIG. 7D α-actinin (green) biomarkers in the cardiomyocytes from the human heart muscle fibers of FIG. 5. Aligned Sarcomere organization was observed from the staining. Nuclei were stained with DAPI.

Figure 8B:
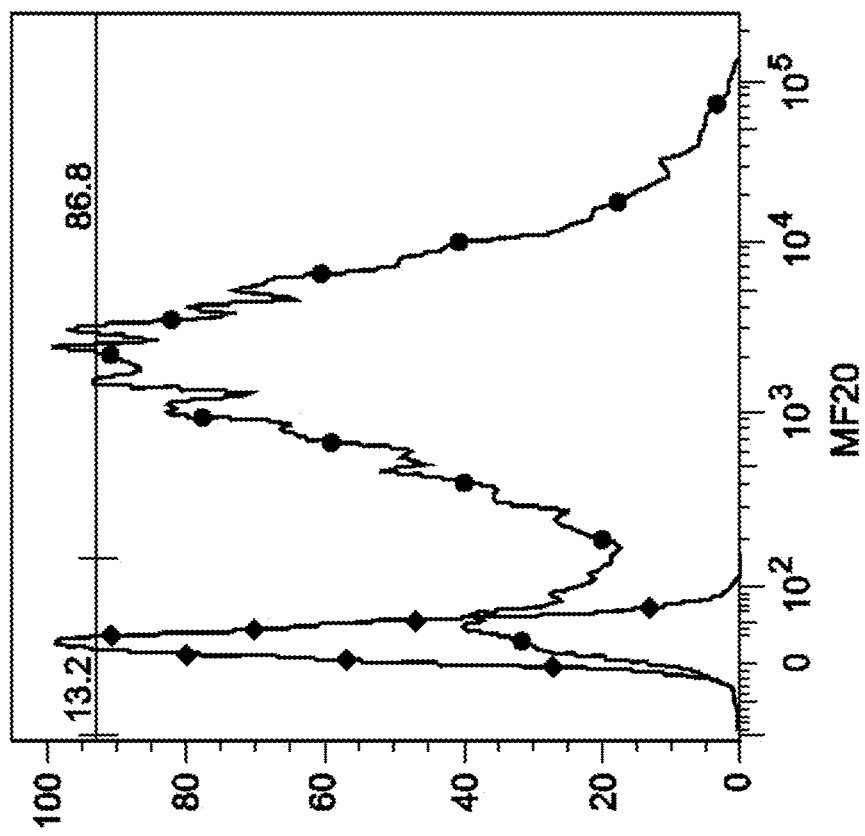
FIGS. 8A-8C show flow cytometry analysis of Day 30 cardiomyocytes.
Figure 8A:
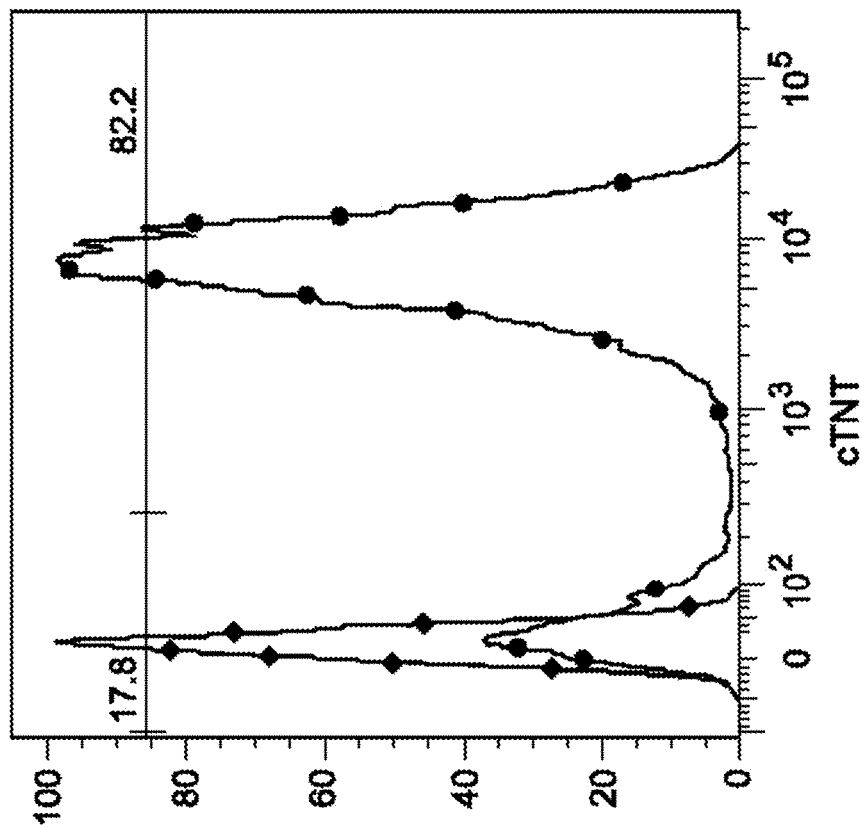
Figure 8C:
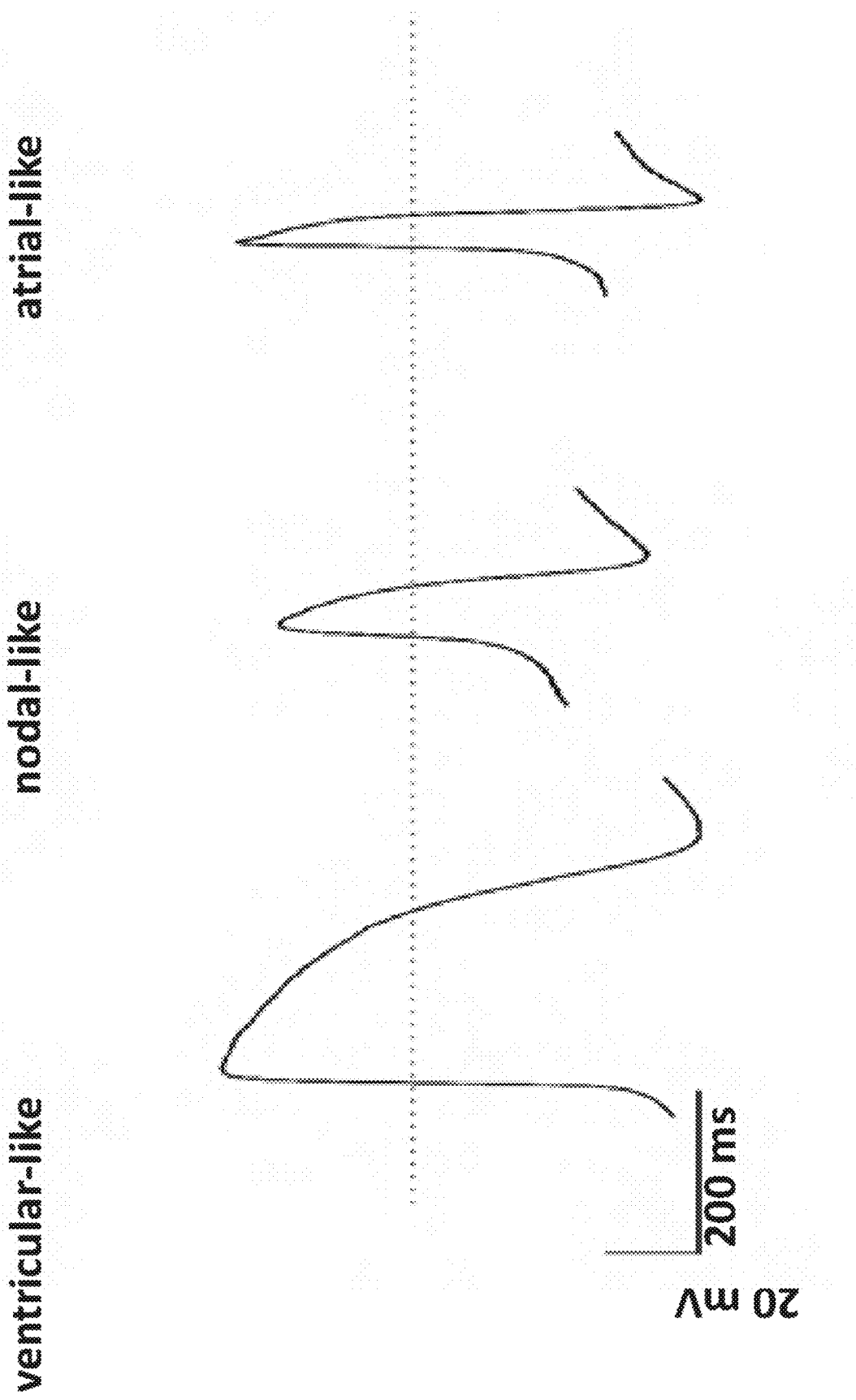

At S118, heart muscle fibers to form muscle fibrils are aligned with each other length-wise into muscle fibrils. The muscle fibrils and aligned muscle fibers are illustrated in the photomicrograph of FIG. 6. At day 20, the beating cardiomyocytes contain cells that mimic heart ventricle, atrium and nodal subtypes as determined by patch clamp analyses (FIG. 8C).

The methods set forth in FIG. 3C may be used to generate cardiomyocytes from hESCs during a period of 14 days under chemically defined, xeno-free conditions and without genetic manipulation. Method S100, particularly at S116, may also be used to develop human heart muscle cells for future regenerative cardiology. In one embodiment, the pluripotent stem cells in Method S100 are hESCs.

Figure 9A:
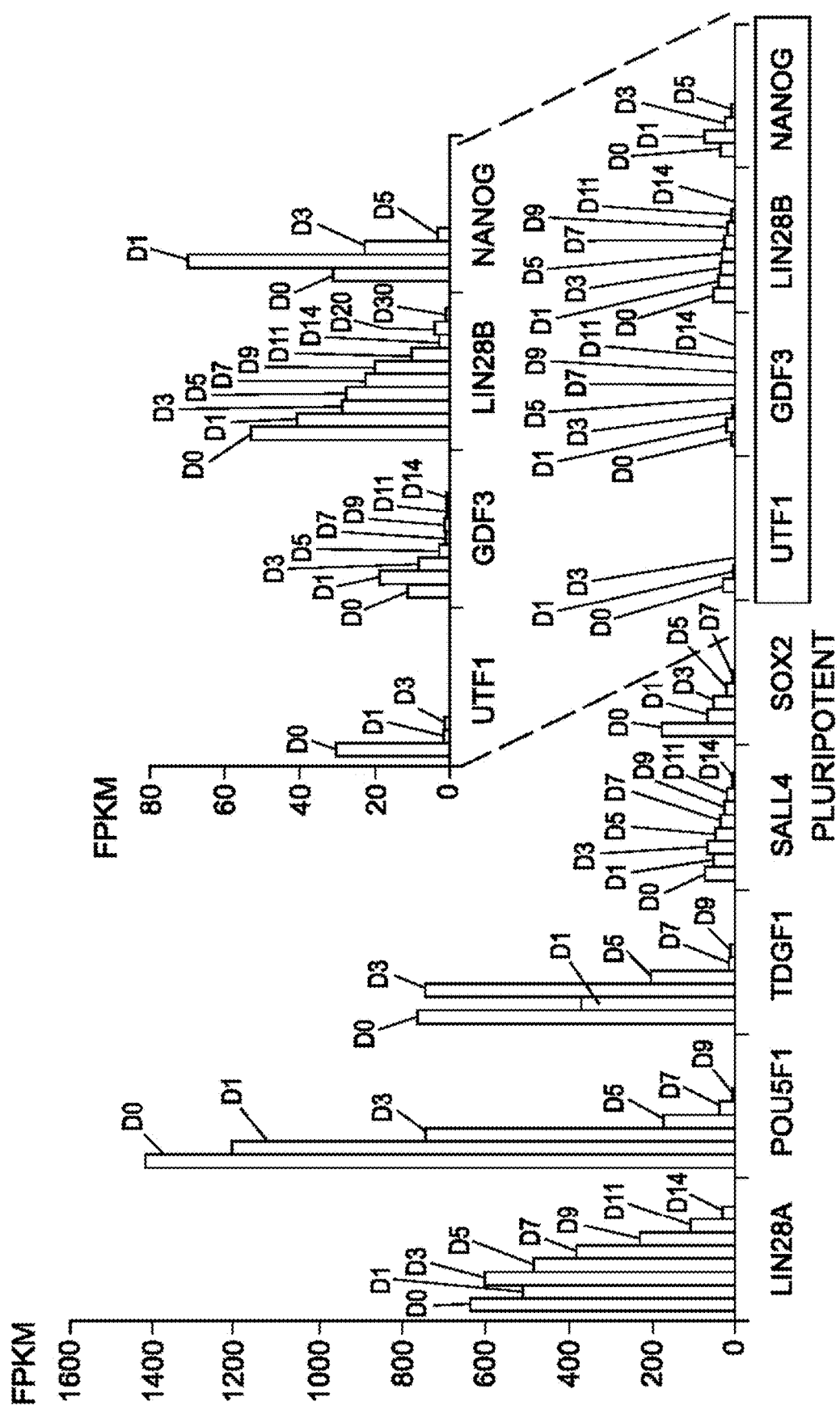
FIGS. 9A-9C include a detailed transcriptome analysis of differentiation days 0, 1, 3, 5, 7, 9, 11, 14, 20 and 30.
Figure 9B:
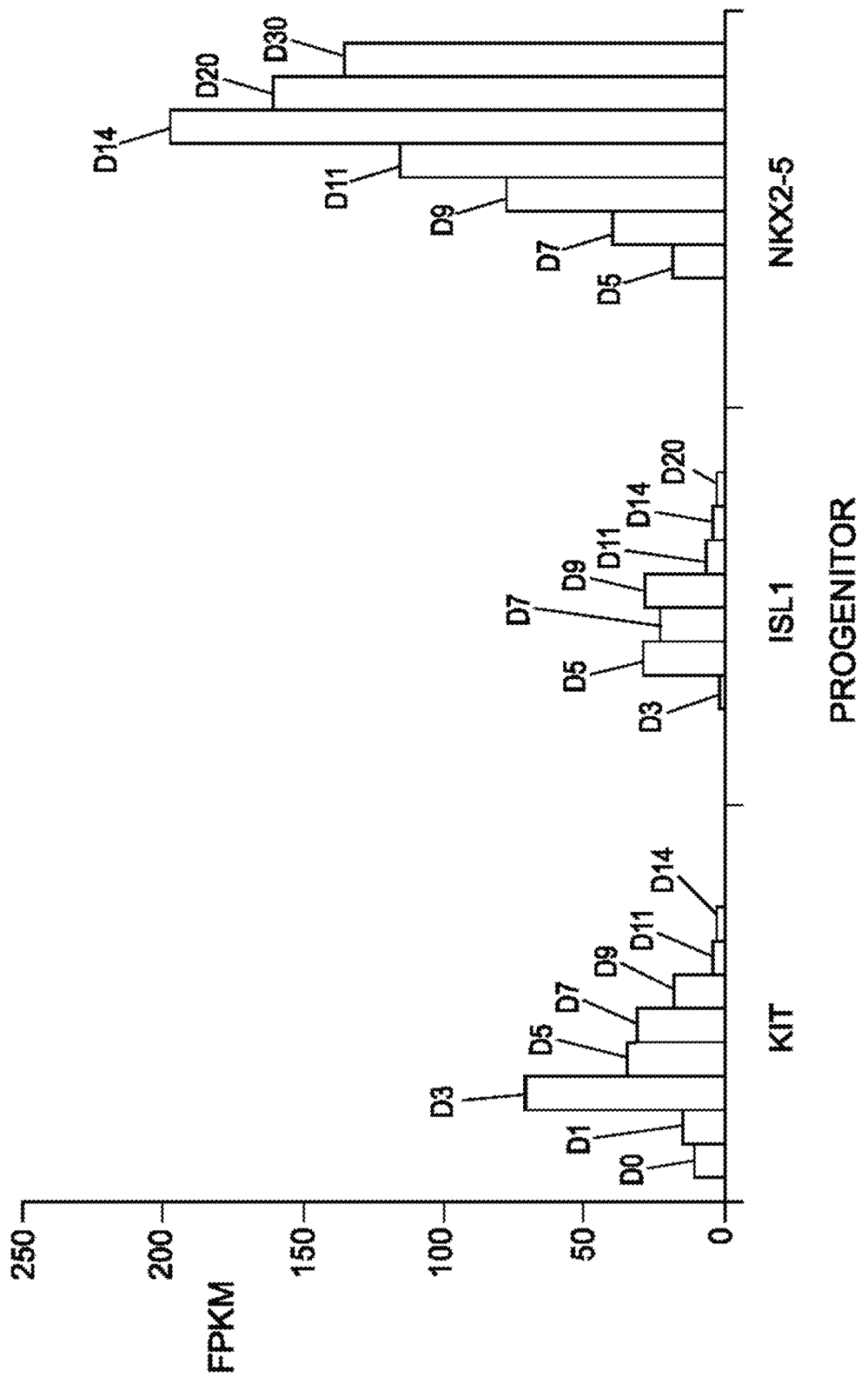
Figure 9C:
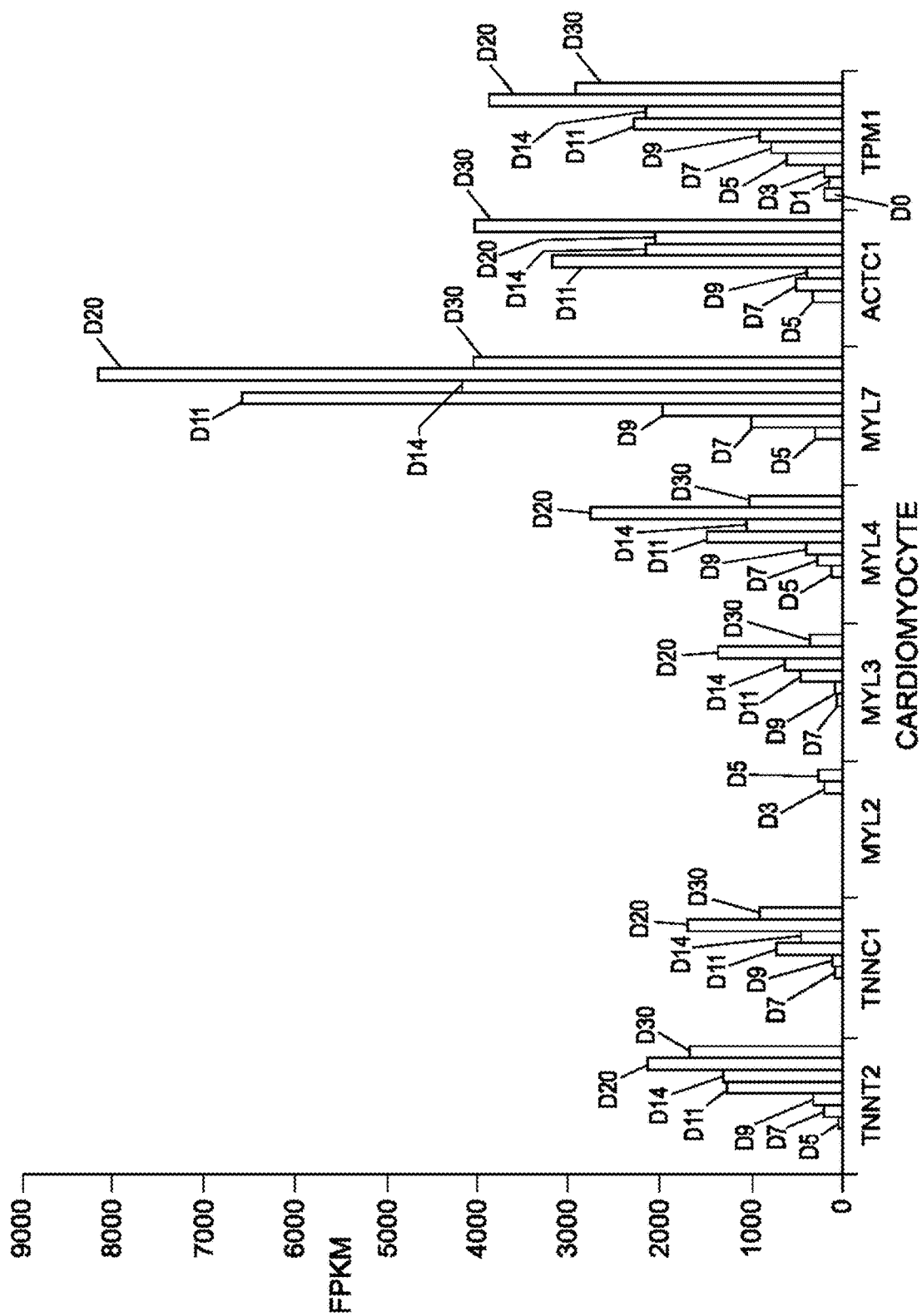

FIG. 9A through FIG. 9C show the levels of various genes during differentiation from days 0 through 30. It is noted that differentiation of cardiomyocytes takes only 14 days, and after that the cells start to mature. These biomarkers can be used to determine how far along in differentiation the stem cells are. FPKM refers to "Fragments Per Kilobase of transcript per Million mapped reads", and is calculated using Cufflinks software. These are relative amounts, which can be used for comparison. As seen in these figures, the amount of LIN28A decreases during differentiation in a relatively linear fashion, as do POU5F1, TDGF1, SALL4, SOX2, UTF1, and LIN28B. The amount of NKX2-5, TNNT2, and MYL3 increase during differentiation. The amounts of NANOG, KIT, ISL1, TNNC1, MYL4, MYL7, ACTC1, and TPM1 increase and peak, then decrease during the 14-day period for differentiation. In FIG. 9C, the amounts of TNNC1, MYL4, MYL7, ACTC1, and TPM1 peak on day 11 of the 14-day differentiation period.

More specifically, the amount of POU5F1 is much greater than LIN28A between days D0 and D3, but then the amount of LIN28A is greater than POU5F1 from days D5 to D14. Similarly, the amount of KIT is greater than ISL1 for days D0 through D7, but the amount of ISL1 is greater than KIT for days D9 through D14. The amount of NKX2-5 is less than ISL1 or KIT up through day D5, but is then greater than both for days D7 through D14. By Day D9, the level of MYL7 is more than twice the level of the proteins MYL3 and MYL4.

The cell culture substrate is used in combination with a cell culture medium. The cell culture medium of the present disclosure is particularly suitable for being used with a substrate that contains (i) laminin-521 or laminin-511 and (ii) laminin-221. Laminins LN-511 and LN-521 activate α6β1 integrins, which in turn leads to activation of the PI3K/Akt pathway. This supports the pluripotency, self-renewal, and/or proliferation of the differentiated cells. It is contemplated that the substrate may consist of laminin-521 or laminin-511, either intact, as separate chains, or as fragments thereof. Recombinant laminin-521 and recombinant laminin-511 are commercially available. Many different molecules can activate the PI3K/Akt pathway, though with different efficiencies. For example, TGF beta 1 and bFGF activate this pathway. The use of laminin-521 and/or laminin-511 allows the quantity of such molecules to be reduced in the cell culture medium. Laminin-521 conveys the highest dose of signal via α6β1 integrin, activating the PI3K/Akt pathway. The use of laminin-521 allows for single-cell suspension passaging without the addition of cell-detrimental rho-kinase (ROCK) inhibitor to increase cell survival after single-cell enzymatic dissociation. Addition of the most abundant cardiomyocyte laminin, LN-221, provides signals that direct the pluripotent hESCs towards the cardiomyocyte lineage, but its mechanism are still unknown.

Typically, cell culture media include a large number and a large amount of various growth factors and cytokines to inhibit differentiation and improve proliferation. One advantage of the cell culture medium of the present disclosure is that it does not contain as many growth factors or cytokines, or such high amounts.

Very generally, the cell culture medium of the present disclosure requires lower amounts of basic fibroblast growth factor (bFGF) than typically used. It is possible that growth promoting domains of the laminin molecules are responsible for this effect. It is contemplated that the cell culture medium may comprise from greater than zero to 3.9 nanograms per milliliter (ng/ml) of bFGF. The bFGF is human bFGF so that the cell culture medium is totally human and defined. In some more specific embodiments, the cell culture medium may comprise 3.5 or lower ng/ml of bFGF. In other embodiments, the cell culture medium may comprise from 0.5 to 3.5 ng/ml of bFGF. In some embodiments, the cell culture medium may have zero bFGF, i.e. no bFGF is present.

Generally, the cell culture medium includes a liquid phase in which at least one inorganic salt, at least one trace mineral, at least one energy substrate, at least one lipid, at least one amino acid, at least one vitamin, and at least one growth factor (besides bFGF) are dissolved. Table 1 below includes a list of various such ingredients which may be present in the cell culture medium of the present disclosure, and the minimum and maximum concentrations if the ingredient is present. The values are presented in scientific notation. For example, "4.1E−01" should be interpreted as $4.1 \times 10^{-01}$.

TABLE 1

| Ingredient | molar mass (g/mol) | Min. Conc. (mM) | Max. Conc. (mM) | Min. Conc. (ng/ml) | Max. Conc. (ng/ml) |
|---|---|---|---|---|---|
| INORGANIC SALTS | | | | | |
| Calcium chloride (Anhydrous) | 110.98 | 4.1E−01 | 1.6E+00 | 4.6E+04 | 1.8E+05 |
| HEPES | 238.3 | 5.9E+00 | 1.8E+01 | 1.4E+06 | 4.2E+06 |
| Lithium Chloride (LiCl) | 42.39 | 4.9E−01 | 1.5E+00 | 2.1E+04 | 6.2E+04 |
| Magnesium chloride (Anhydrous) | 95.21 | 1.2E−01 | 3.6E−01 | 1.1E+04 | 3.4E+04 |
| Magnesium Sulfate (MgSO$_4$) | 120.37 | 1.6E−01 | 4.8E−01 | 1.9E+04 | 5.8E+04 |
| Potassium chloride (KCl) | 74.55 | 1.6E+00 | 4.9E+00 | 1.2E+05 | 3.6E+05 |
| Sodium bicarbonate (NaHCO$_3$) | 84.01 | 9.0E+00 | 4.4E+01 | 7.6E+05 | 3.7E+06 |
| Sodium chloride (NaCl) | 58.44 | 4.7E+01 | 1.4E+02 | 2.8E+06 | 8.3E+06 |
| Sodium phosphate, dibasic (Anhydrous) | 141.96 | 2.0E−01 | 5.9E−01 | 2.8E+04 | 8.3E+04 |
| Sodium phosphate, monobasic monohydrate (NaH$_2$PO$_4$-H$_2$O) | 137.99 | 1.8E−01 | 5.3E−01 | 2.4E+04 | 7.3E+04 |
| TRACE MINERALS | | | | | |
| Ferric Nitrate (Fe(NO$_3$)$_3$-9H$_2$O) | 404 | 4.9E−05 | 1.9E−04 | 2.0E+01 | 7.5E+01 |
| Ferrous sulfate heptahydrate (FeSO$_4$-7H$_2$O) | 278.01 | 5.9E−04 | 1.8E−03 | 1.6E+02 | 4.9E+02 |
| Copper(II) sulfate pentahydrate (CuSO$_4$-5H$_2$O) | 249.69 | 2.0E−06 | 8.0E−06 | 5.1E−01 | 2.0E+00 |
| Zinc sulfate heptahydrate (ZnSO$_4$-7H$_2$O) | 287.56 | 5.9E−04 | 1.8E−03 | 1.7E+02 | 5.1E+02 |
| Ammonium Metavanadate NH$_4$VO$_3$ | 116.98 | 5.5E−06 | 1.6E−05 | 6.4E−01 | 1.9E+00 |
| Manganese Sulfate monohydrate (MnSO$_4$-H$_2$O) | 169.02 | 9.9E−07 | 3.0E−06 | 1.7E−01 | 5.0E−01 |
| NiSO$_4$-6H$_2$O | 262.85 | 4.9E−07 | 1.5E−06 | 1.3E−01 | 3.8E−01 |
| Selenium | 78.96 | 8.9E−05 | 2.7E−04 | 7.0E+00 | 2.1E+01 |
| Sodium Meta Silicate Na$_2$SiO$_3$-9H$_2$O | 284.2 | 4.8E−04 | 1.4E−03 | 1.4E+02 | 4.1E+02 |
| SnCl$_2$ | 189.62 | 6.2E−07 | 1.9E−06 | 1.2E−01 | 3.5E−01 |
| Molybdic Acid, Ammonium salt | 1235.86 | 9.9E−07 | 3.0E−06 | 1.2E+00 | 3.7E+00 |
| CdCl$_2$ | 183.32 | 6.1E−06 | 1.8E−05 | 1.1E+00 | 3.4E+00 |
| CrCl$_3$ | 158.36 | 9.9E−07 | 3.0E−06 | 1.6E−01 | 4.7E−01 |
| AgNO$_3$ | 169.87 | 4.9E−07 | 1.5E−06 | 8.3E−02 | 2.5E−01 |
| AlCl$_3$-6H$_2$O | 241.43 | 2.4E−06 | 7.3E−06 | 5.9E−01 | 1.8E+00 |

TABLE 1-continued

| Ingredient | molar mass (g/mol) | Min. Conc. (mM) | Max. Conc. (mM) | Min. Conc. (ng/ml) | Max. Conc. (ng/ml) |
|---|---|---|---|---|---|
| Barium Acetate (Ba(C$_2$H$_3$O$_2$)$_2$) | 255.42 | 4.9E−06 | 1.5E−05 | 1.3E+00 | 3.8E+00 |
| CoCl$_2$-6H$_2$O | 237.93 | 4.9E−06 | 1.5E−05 | 1.2E+00 | 3.5E+00 |
| GeO$_2$ | 104.64 | 2.5E−06 | 7.5E−06 | 2.6E−01 | 7.8E−01 |
| KBr | 119 | 4.9E−07 | 1.5E−06 | 5.9E−02 | 1.8E−01 |
| KI | 166 | 5.0E−07 | 1.5E−06 | 8.3E−02 | 2.5E−01 |
| NaF | 41.99 | 4.9E−05 | 1.5E−04 | 2.1E+00 | 6.2E+00 |
| RbCl | 120.92 | 4.9E−06 | 1.5E−05 | 5.9E−01 | 1.8E+00 |
| ZrOCl$_2$-8H$_2$O | 178.13 | 4.9E−06 | 1.5E−05 | 8.7E−01 | 2.6E+00 |
| ENERGY SUBSTRATES | | | | | |
| D-Glucose | 180.16 | 6.9E+00 | 2.1E+01 | 1.2E+06 | 3.7E+06 |
| Sodium Pyruvate | 110.04 | 2.0E−01 | 5.9E−01 | 2.2E+04 | 6.5E+04 |
| LIPIDS | | | | | |
| Linoleic Acid | 280.45 | 9.4E−05 | 2.8E−04 | 2.6E+01 | 7.9E+01 |
| Lipoic Acid | 206.33 | 2.0E−04 | 7.8E−04 | 4.1E+01 | 1.6E+02 |
| Arachidonic Acid | 304.47 | 6.5E−06 | 1.9E−05 | 2.0E+00 | 5.9E+00 |
| Cholesterol | 386.65 | 5.6E−04 | 1.7E−03 | 2.2E+02 | 6.5E+02 |
| DL-alpha tocopherol-acetate | 472.74 | 1.5E−04 | 4.4E−04 | 6.9E+01 | 2.1E+02 |
| Linolenic Acid | 278.43 | 3.5E−05 | 1.0E−04 | 9.7E+00 | 2.9E+01 |
| Myristic Acid | 228.37 | 4.3E−05 | 1.3E−04 | 9.8E+00 | 2.9E+01 |
| Oleic Acid | 282.46 | 3.5E−05 | 1.0E−04 | 9.8E+00 | 2.9E+01 |
| Palmitic Acid | 256.42 | 3.8E−05 | 1.1E−04 | 9.8E+00 | 2.9E+01 |
| Palmitoleic acid | 254.408 | 3.9E−05 | 1.2E−04 | 9.8E+00 | 2.9E+01 |
| Stearic Acid | 284.48 | 3.4E−05 | 1.0E−04 | 9.8E+00 | 2.9E+01 |
| AMINO ACIDS | | | | | |
| L-Alanine | 89.09 | 2.5E−02 | 2.1E−01 | 2.2E+03 | 1.8E+04 |
| L-Arginine hydrochloride | 147.2 | 2.7E−01 | 1.5E+00 | 4.0E+04 | 2.2E+05 |
| L-Asparagine-H$_2$O | 150.13 | 5.0E−02 | 2.1E−01 | 7.5E+03 | 3.1E+04 |
| L-Aspartic acid | 133.1 | 2.5E−02 | 2.1E−01 | 3.3E+03 | 2.7E+04 |
| L-Cysteine-HCl-H$_2$O | 175.63 | 3.9E−02 | 1.2E−01 | 6.9E+03 | 2.1E+04 |
| L-Cystine dihydrochloride | 313.22 | 3.9E−02 | 1.2E−01 | 1.2E+04 | 3.7E+04 |
| L-Glutamic acid | 147.13 | 2.5E−02 | 2.1E−01 | 3.7E+03 | 3.0E+04 |
| L-Glutamine | 146.15 | 1.5E+00 | 4.4E+00 | 2.1E+05 | 6.4E+05 |
| Glycine | 75.07 | 1.5E−01 | 4.4E−01 | 1.1E+04 | 3.3E+04 |
| L-Histidine monohydrochloride monohydrate | 209.63 | 5.9E−02 | 1.8E−01 | 1.2E+04 | 3.7E+04 |
| L-Isoleucine | 131.17 | 1.6E−01 | 4.9E−01 | 2.1E+04 | 6.4E+04 |
| L-Leucine | 131.17 | 1.8E−01 | 5.3E−01 | 2.3E+04 | 7.0E+04 |
| L-Lysine hydrochloride | 182.65 | 2.0E−01 | 5.9E−01 | 3.6E+04 | 1.1E+05 |
| L-Methionine | 149.21 | 4.5E−02 | 1.4E−01 | 6.8E+03 | 2.0E+04 |
| L-Phenylalanine | 165.19 | 8.5E−02 | 2.5E−01 | 1.4E+04 | 4.2E+04 |
| L-Proline | 115.13 | 1.1E−01 | 3.2E−01 | 1.2E+04 | 3.7E+04 |
| L-Serine | 105.09 | 1.5E−01 | 4.4E−01 | 1.5E+04 | 4.6E+04 |
| L-Threonine | 119.12 | 1.8E−01 | 5.3E−01 | 2.1E+04 | 6.3E+04 |
| L-Tryptophan | 204.23 | 1.7E−02 | 5.2E−02 | 3.5E+03 | 1.1E+04 |
| L-Tyrosine disodium salt hydrate | 225.15 | 8.4E−02 | 3.7E−01 | 1.9E+04 | 8.4E+04 |
| L-Valine | 117.15 | 1.8E−01 | 5.3E−01 | 2.1E+04 | 6.2E+04 |
| VITAMINS | | | | | |
| Ascorbic acid | 176.12 | 1.3E−01 | 3.8E−01 | 2.2E+04 | 6.7E+04 |
| Biotin | 244.31 | 5.6E−06 | 1.7E−05 | 1.4E+00 | 4.1E+00 |
| B$_{12}$ | 1355.37 | 2.0E−04 | 5.9E−04 | 2.7E+02 | 8.0E+02 |
| Choline chloride | 139.62 | 2.5E−02 | 7.5E−02 | 3.5E+03 | 1.1E+04 |
| D-Calcium pantothenate | 238.27 | 1.8E−03 | 1.4E−02 | 4.4E+02 | 3.4E+03 |
| Folic acid | 441.4 | 2.4E−03 | 7.1E−03 | 1.0E+03 | 3.1E+03 |
| i-Inositol | 180.16 | 2.7E−02 | 1.1E−01 | 4.9E+03 | 1.9E+04 |
| Niacinamide | 122.12 | 6.5E−03 | 2.0E−02 | 7.9E+02 | 2.4E+03 |
| Pyridoxine hydrochloride | 205.64 | 3.8E−03 | 1.1E−02 | 7.8E+02 | 2.4E+03 |
| Riboflavin | 376.36 | 2.3E−04 | 6.8E−04 | 8.6E+01 | 2.6E+02 |
| Thiamine hydrochloride | 337.27 | 3.3E−03 | 3.6E−02 | 1.1E+03 | 1.2E+04 |
| GROWTH FACTORS/PROTEINS | | | | | |
| GABA | 103.12 | 0 | 1.5E+00 | 0 | 1.5E+05 |
| Pipecolic Acid | 129 | 0 | 1.5E−03 | 0 | 1.9E+02 |
| bFGF | 18000 | 0 | 2.17E−07 | 0 | 3.9E+00 |
| TGF beta 1 | 25000 | 0 | 3.5E−08 | 0 | 8.8E−01 |
| Human Insulin | 5808 | 0 | 5.9E−03 | 0 | 3.4E+04 |
| Human Holo-Transferrin | 78500 | 0 | 2.1E−04 | 0 | 1.6E+04 |
| Human Serum Albumin | 67000 | 0 | 2.9E−01 | 0 | 2.0E+07 |
| Glutathione (reduced) | 307.32 | 0 | 9.6E−03 | 0 | 2.9E+03 |
| OTHER COMPONENTS | | | | | |
| Hypoxanthine Na | 136.11 | 5.9E−03 | 2.6E−02 | 8.0E+02 | 3.6E+03 |
| Phenol red | 354.38 | 8.5E−03 | 2.5E−02 | 3.0E+03 | 9.0E+03 |
| Putrescine-2HCl | 161.07 | 2.0E−04 | 5.9E−04 | 3.2E+01 | 9.5E+01 |
| Thymidine | 242.229 | 5.9E−04 | 1.8E−03 | 1.4E+02 | 4.3E+02 |
| 2-mercaptoethanol | 78.13 | 4.9E−02 | 1.5E−01 | 3.8E+03 | 1.1E+04 |
| Pluronic F-68 | 8400 | 1.2E−02 | 3.5E−02 | 9.8E+04 | 2.9E+05 |
| Tween 80 | 1310 | 1.6E−04 | 4.9E−04 | 2.2E+02 | 6.5E+02 |

The liquid phase of the cell culture medium may be water, serum, or albumin.

Many of the ingredients or components listed above in Table 1 are not necessary, or can be used in lower concentrations.

It is contemplated that the cell culture medium may contain insulin or an insulin substitute. Similarly, the cell culture medium may contain transferrin or a transferrin substitute. However, in more specific embodiments, it is contemplated that the cell culture medium may not contain (1) insulin or insulin substitute, or (2) transferrin or transferrin substitute, or any combination of these two components. Alternatively, in other embodiments, it is contemplated that the cell culture medium may contain (1) insulin or insulin substitute, or (2) transferrin or transferrin substitute, or any combination of these two components.

It should be noted that other cell culture media may contain growth factors such as interleukin-1 beta (IL-β or catabolin), interleukin-6 (IL6), or pigment epithelium derived factor (PEDF). Such growth factors are not present in the cell culture medium of the present disclosure.

One specific formula for a cell culture medium is provided in Table 2:

TABLE 2

| Ingredient | Amount | Unit |
|---|---|---|
| bFGF | 0.39 | microgram (µg) |
| Albumin | 1.34 | milligram (mg) |
| Insulin | 2 | mg |
| Lithium Chloride | 4.23 | mg |
| GABA | 0.01 | mg |
| TGF beta 1 | 0.06 | µg |
| Pipecolic acid | 0.013 | mg |
| L-glutamine | 2.92 | grams |
| MEM non-essential amino acid solution | 1 | mL |
| DMEM/F12 | 100 | mL |

In this regard, MEM non-essential amino acid solution is typically provided in a 100× concentrate. The MEM of Table 2 is used after dilution back to 1×, and contains the following amino acids in the following concentration listed in Table 3:

TABLE 3

| MEM Amino Acids | Concentration (ng/ml) |
|---|---|
| Glycine | 7.50E+03 |
| L-Alanine | 8.90E+03 |
| L-Asparagine | 1.32E+04 |
| L-Aspartic acid | 1.33E+04 |
| L-Proline | 1.15E+04 |
| L-Serine | 1.05E+04 |

DMEM/F12 contains the following ingredients listed in Table 4:

TABLE 4

| DMEM/F12 Ingredients | Concentration (ng/ml) |
|---|---|
| Glycine | 187.5 |
| L-Alanine | 44.5 |
| L-Arginine hydrochloride | 1475 |
| L-Asparagine-$H_2O$ | 75 |
| L-Aspartic acid | 66.5 |
| L-Cysteine hydrochloride-$H_2O$ | 175.6 |
| L-Cystine 2HCl | 312.9 |
| L-Glutamic Acid | 73.5 |
| L-Glutamine | 3650 |
| L-Histidine hydrochloride-$H_2O$ | 314.8 |
| L-Isoleucine | 544.7 |
| L-Leucine | 590.5 |
| L-Lysine hydrochloride | 912.5 |
| L-Methionine | 172.4 |
| L-Phenylalanine | 354.8 |
| L-Proline | 172.5 |
| L-Serine | 262.5 |
| L-Threonine | 534.5 |
| L-Tryptophan | 90.2 |
| L-Tyrosine disodium salt dihydrate | 557.9 |
| L-Valine | 528.5 |
| Biotin | 0.035 |
| Choline chloride | 89.8 |
| D-Calcium pantothenate | 22.4 |
| Folic Acid | 26.5 |
| Niacinamide | 20.2 |
| Pyridoxine hydrochloride | 20 |
| Riboflavin | 2.19 |
| Thiamine hydrochloride | 21.7 |
| Vitamin $B_{12}$ | 6.8 |
| i-Inositol | 126 |
| Calcium Chloride ($CaCl_2$) (anhyd.) | 1166 |
| Cupric sulfate ($CuSO_4$-$5H_2O$) | 0.013 |
| Ferric Nitrate ($Fe(NO_3)_3$-$9H_2O$) | 0.5 |
| Ferric sulfate ($FeSO_4$-$7H_2O$) | 4.17 |
| Magnesium Chloride (anhydrous) | 286.4 |
| Magnesium Sulfate ($MgSO_4$) (anhyd.) | 488.4 |
| Potassium Chloride (KCl) | 3118 |
| Sodium Bicarbonate ($NaHCO_3$) | 24380 |
| Sodium Chloride (NaCl) | 69955 |
| Sodium Phosphate dibasic ($Na_2HPO_4$) anhydrous | 710.2 |
| Sodium Phosphate monobasic ($NaH_2PO_4$-$H_2O$) | 625 |
| Zinc sulfate ($ZnSO_4$-$7H_2O$) | 4.32 |
| D-Glucose (Dextrose) | 31510 |
| Hypoxanthine Na | 23.9 |
| Linoleic Acid | 0.42 |
| Lipoic Acid | 1.05 |
| Phenol Red | 81 |
| Putrescine 2HCl | 0.81 |
| Sodium Pyruvate | 550 |
| Thymidine | 3.65 |

In particular, the cell culture medium may have an albumin concentration of at least 0.3 millimolar (mM). Table 5 below provides a formulation for a cell culture medium containing additional albumin.

In particular embodiments, the amount of human serum albumin (HSA) can be varied from a concentration of 0.195 mM to 1 mM, including from 0.3 mM to 1 mM or from 0.3 mM to about 0.4 mM. The amount of bFGF can also be varied from 0 to about 105 ng/ml, or from 0 to 3.9 ng/ml, or from 0.5 ng/ml to 3.5 ng/ml. These two variations in the amount of HSA and bFGF may occur independently or together.

TABLE 5 mTeSR1 formulation.

| mTeSR1 Ingredient | molar mass (g/mol) | Concentration (ng/ml) | Concentration (mM) |
|---|---|---|---|
| INORGANIC SALTS | | | |
| Calcium chloride (Anhydrous) | 110.98 | 9.14E+04 | 8.24E−01 |
| HEPES | 238.3 | 2.81E+06 | 1.18E+01 |
| Lithium Chloride (LiCl) | 42.39 | 4.15E+04 | 9.80E−01 |
| Magnesium chloride (Anhydrous) | 95.21 | 2.26E+04 | 2.37E−01 |
| Magnesium Sulfate ($MgSO_4$) | 120.37 | 3.84E+04 | 3.19E−01 |
| Potassium chloride (KCl) | 74.55 | 2.43E+05 | 3.26E+00 |
| Sodium bicarbonate ($NaHCO_3$) | 84.01 | 1.51E+06 | 1.80E+01 |
| Sodium chloride (NaCl) | 58.44 | 5.53E+06 | 9.46E+01 |
| Sodium phosphate, dibasic (Anhydrous) | 141.96 | 5.56E+04 | 3.92E−01 |
| Sodium phosphate, monobasic monohydrate ($NaH_2PO_4$-$H_2O$) | 137.99 | 4.90E+04 | 3.55E−01 |
| TRACE MINERALS | | | |
| Ferric Nitrate ($Fe(NO_3)_3$-$9H_2O$) | 404 | 3.92E+01 | 9.71E−05 |
| Ferrous sulfate heptahydrate ($FeSO_4$-$7H_2O$) | 278.01 | 3.28E+02 | 1.18E−03 |
| Copper(II) sulfate pentahydrate ($CuSO_4$-$5H_2O$) | 249.69 | 1.02E+00 | 4.08E−06 |
| Zinc sulfate heptahydrate ($ZnSO_4$-$7H_2O$) | 287.56 | 3.39E+02 | 1.18E−03 |
| Ammonium Metavanadate $NH_4VO_3$ | 116.98 | 1.28E+00 | 1.09E−05 |
| Manganese Sulfate monohydrate ($MnSO_4$-$H_2O$) | 169.02 | 3.33E−01 | 1.97E−06 |
| $NiSO_4$-$6H_2O$ | 262.85 | 2.55E−01 | 9.70E−07 |
| Selenium | 78.96 | 1.40E+01 | 1.77E−04 |
| Sodium Meta Silicate $Na_2SiO_3$ $9H_2O$ | 284.2 | 2.75E+02 | 9.66E−04 |
| $SnCl_2$ | 189.62 | 2.35E−01 | 1.24E−06 |
| Molybdic Acid, Ammonium salt | 1235.86 | 2.43E+00 | 1.97E−06 |
| $CdCl_2$ | 183.32 | 2.24E+00 | 1.22E−05 |
| $CrCl_3$ | 158.36 | 3.14E−01 | 1.98E−06 |
| $AgNO_3$ | 169.87 | 1.67E−01 | 9.81E−07 |
| $AlCl_3$ $6H_2O$ | 241.43 | 1.18E+00 | 4.87E−06 |
| Barium Acetate ($Ba(C_2H_3O_2)_2$) | 255.42 | 2.50E+00 | 9.79E−06 |
| $CoCl_2$ $6H_2O$ | 237.93 | 2.33E+00 | 9.81E−06 |
| $GeO_2$ | 104.64 | 5.20E−01 | 4.97E−06 |
| KBr | 119 | 1.18E−01 | 9.89E−07 |
| KI | 166 | 1.66E−01 | 1.00E−06 |
| NaF | 41.99 | 4.13E+00 | 9.83E−05 |
| RbCl | 120.92 | 1.19E+00 | 9.81E−06 |
| $ZrOCl_2$ $8H_2O$ | 178.13 | 1.75E+00 | 9.80E−06 |
| ENERGY SUBSTRATES | | | |
| D-Glucose | 180.16 | 2.47E+06 | 1.37E+01 |
| Sodium Pyruvate | 110.04 | 4.31E+04 | 3.92E−01 |
| LIPIDS | | | |
| Linoleic Acid | 280.45 | 5.27E+01 | 1.88E−04 |
| Lipoic Acid | 206.33 | 8.25E+01 | 4.00E−04 |
| Arachidonic Acid | 304.47 | 3.93E+00 | 1.29E−05 |
| Cholesterol | 386.65 | 4.33E+02 | 1.12E−03 |
| DL-alpha tocopherol-acetate | 472.74 | 1.37E+02 | 2.90E−04 |
| Linolenic Acid | 278.43 | 1.95E+01 | 6.99E−05 |
| Myristic Acid | 228.37 | 1.96E+01 | 8.59E−05 |
| Oleic Acid | 282.46 | 1.96E+01 | 6.94E−05 |

TABLE 5-continued mTeSR1 formulation.

| mTeSR1 Ingredient | molar mass (g/mol) | Concentration (ng/ml) | Concentration (mM) |
|---|---|---|---|
| Palmitic Acid | 256.42 | 1.96E+01 | 7.65E−05 |
| Palmitoleic acid | 254.408 | 1.96E+01 | 7.71E−05 |
| Stearic Acid | 284.48 | 1.96E+01 | 6.89E−05 |
| AMINO ACIDS | | | |
| L-Alanine | 89.09 | 1.22E+04 | 1.37E−01 |
| L-Arginine hydrochloride | 147.2 | 8.07E+04 | 5.48E−01 |
| L-Asparagine-H$_2$O | 150.13 | 2.06E+04 | 1.37E−01 |
| L-Aspartic acid | 133.1 | 1.82E+04 | 1.37E−01 |
| L-Cysteine-HCl-H$_2$O | 175.63 | 1.38E+04 | 7.83E−02 |
| L-Cystine dihydrochloride | 313.22 | 2.45E+04 | 7.83E−02 |
| L-Glutamic acid | 147.13 | 2.02E+04 | 1.37E−01 |
| L-Glutamine | 146.15 | 4.30E+05 | 2.94E+00 |
| Glycine | 75.07 | 2.21E+04 | 2.94E−01 |
| L-Histidine monohydrochloride monohydrate | 209.63 | 2.47E+04 | 1.18E−01 |
| L-Isoleucine | 131.17 | 4.28E+04 | 3.26E−01 |
| L-Leucine | 131.17 | 4.64E+04 | 3.54E−01 |
| L-Lysine hydrochloride | 182.65 | 7.14E+04 | 3.91E−01 |
| L-Methionine | 149.21 | 1.35E+04 | 9.06E−02 |
| L-Phenylalanine | 165.19 | 2.79E+04 | 1.69E−01 |
| L-Proline | 115.13 | 2.49E+04 | 2.16E−01 |
| L-Serine | 105.09 | 3.09E+04 | 2.94E−01 |
| L-Threonine | 119.12 | 4.19E+04 | 3.52E−01 |
| L-Tryptophan | 204.23 | 7.07E+03 | 3.46E−02 |
| L-Tyrosine disodium salt hydrate | 225.15 | 3.78E+04 | 1.68E−01 |
| L-Valine | 117.15 | 4.16E+04 | 3.55E−01 |
| VITAMINS | | | |
| Ascorbic acid | 176.12 | 4.46E+04 | 2.53E−01 |
| Biotin | 244.31 | 2.74E+00 | 1.12E−05 |
| B12 | 1355.37 | 5.34E+02 | 3.94E−04 |
| Choline chloride | 139.62 | 7.02E+03 | 5.03E−02 |
| D-Calcium pantothenate | 238.27 | 8.79E+02 | 3.69E−03 |
| Folic acid | 441.4 | 2.08E+03 | 4.71E−03 |
| i-Inositol | 180.16 | 9.89E+03 | 5.49E−02 |
| Niacinamide | 122.12 | 1.59E+03 | 1.30E−02 |
| Pyridoxine hydrochloride | 205.64 | 1.57E+03 | 7.62E−03 |
| Riboflavin | 376.36 | 1.72E+02 | 4.56E−04 |
| Thiamine hydrochloride | 337.27 | 8.16E+03 | 2.42E−02 |
| GROWTH FACTORS/PROTEINS | | | |
| GABA | 103.12 | 1.01E+05 | 9.79E−01 |
| Pipecolic Acid | 129 | 1.27E+02 | 9.84E−04 |
| bFGF | 18000 | 1.04E+02 | 5.77E−06 |
| TGF beta 1 | 25000 | 5.88E−01 | 2.35E−08 |
| Human Insulin | 5808 | 2.28E+04 | 3.92E−03 |
| Human Holo-Transferrin | 78500 | 1.08E+04 | 1.37E−04 |
| Human Serum Albumin | 67000 | 1.31E+07 | 1.95E−01 |
| Glutathione (reduced) | 307.32 | 1.96E+03 | 6.38E−03 |
| OTHER COMPONENTS | | | |
| Hypoxanthine Na | 136.11 | 1.61E+03 | 1.18E−02 |
| Phenol red | 354.38 | 5.99E+03 | 1.69E−02 |
| Putrescine-2HCl | 161.07 | 6.36E+01 | 3.95E−04 |
| Thymidine | 242.229 | 2.86E+02 | 1.18E−03 |
| 2-mercaptoethanol | 78.13 | 7.66E+03 | 9.80E−02 |
| Pluronic F-68 | 8400 | 1.96E+05 | 2.33E−02 |
| Tween 80 | 1310 | 4.31E+02 | 3.29E−04 |

The combination of the laminin substrate with the cell culture medium of the present disclosure results in a cell culture system that can be cheaper yet provides higher efficiency in maintaining differentiated cells. In essence, all that is required is specific laminins and a minimal amount of nutrition. It is particularly contemplated that the laminin used in combination with this cell culture medium is either LN-511 or LN-521 in combination with LN-221.

The cell culture system in some embodiments includes a combination cell culture substrate with (i) laminin-221 and (ii) one of laminin-511 or laminin-521, and maintains differentiated human cardiomyocytes longer than shown by conventional fibronectin substrates.

The method of differentiating cardiomyocytes from pluripotent stem cells as described represents the first time a differentiation protocol for hES cells that generates in a controllable fashion Islet-1 positive progenitors, and then subsequently, TnT cardiomyocytes that express regular beatings in vitro. The laminins 521, 511, and 221 used in the method can be produced under GMP conditions such that they form appropriate human substrata for derivation, expansion and differentiation of cells for regenerative medicine. The method can be carried out without the presence of any animal-derived molecules which is important from the point of view of developing cardiac progenitors and differentiated cardiomyocytes for human cell therapy purposes or for testing the effects of drugs on human cardiomyocytes.

Translation of the method for differentiating cardiomyocytes to industrial applications may include industrial production of GMP quality LN-221. Using the method, it will be possible to produce large quantities of hES cell derived cardiac progenitors and cardiomyocytes required for cell therapy of heart muscle injury. This production of the cells may require culturing on (i) human LN-521 or LN-511 and (ii) LN-221. The method provides significant advances for production of human cardiac progenitor cells and cardiomyocytes for cardiotoxicity and drug testing. The pharmaceutical industry is currently struggling with a low rate of new drug candidates, long discovery processes, increasing developmental costs and high attrition rates during later stages of drug development.

Current cell systems used in research and development are hampered by the fact that primary cells or cell lines either rapidly lose important functional systems, or already lack these properties. This may limit their use for validation of pharmacokinetic properties or predicting unexpected toxicity. Moreover, many human primary cell types, such as cardiomyocytes and neuronal cells, are almost inaccessible for these applications. The animal-based in vivo and in vitro systems used within drug discovery are neither cost effective nor clinical relevant or predictive due to the low concordance between animal data and man. There is a strong need for new, innovative cell assays with high human relevance where new candidate drugs can be validated. Human pluripotent stem cells which have been effectively differentiated into the functional cells possess a virtually unlimited supply of cells with a broad variety of applications, spanning from pharmaceutical development to direct use in human cell therapies.

The following examples are for purposes of further illustrating the present disclosure. The examples are merely illustrative and are not intended to limit devices made in accordance with the disclosure to the materials, conditions, or process parameters set forth therein.

EXAMPLES

Example 1: Identification of LN-521 or LN-511 and LN-221 for Combination Substrate Used in Differentiating Cardiomyocyte Cells The described method for differentiating cardiomyocytes from human pluripotent stem cells includes two specific human laminin isoforms (i) LN-521 or LN-511 and (ii) LN-221 that, based on expression analysis of human heart muscle, could be considered important as cell culture substrata. Based on mRNA analysis, laminin chains, alpha-2, beta-2 and gamma-1 are the most highly expressed alpha, beta and gamma laminin chains in the mature cardiac muscle. The alpha-5 and beta-1 chains are less abundant, and alpha-1, alpha-3, beta-3, beta-4, gamma-2 and gamma-3 exhibit low or no detectable expression. It is therefore hypothesized, without being held to any particular theory that LN-221, which has the highest expression, is of major importance for the development and maintenance of cardiomyocyte phenotype and function.

To test this hypothesis, full-length cDNAs for the human laminin chains, alpha-2, beta-2 and gamma-1, were inserted into human expression vectors after which HEK293 (human embryonic kidney) cells were sequentially transfected, clone-selected and expanded as previously described for LN-511. Further information on the process previously described for LN-511 is found in Doi, M., Thyboll, J., Kortesmaa, J., Jansson, K., Iivanainen, A., Parvardeh, M., Timpl, R., Hedin, U., Swedenborg, J., and Tryggvason, K. 2002. Recombinant human laminin-10 (LN-511). Production, purification, and migration-promoting activity on vascular endothelial cells. *J Biol Chem* 277:12741-12748, which is incorporated by reference. A cell line expressing high amounts of trimeric LN-221 produced as recombinant was selected for production of LN-221. Recombinant LN-221 was used together with the highly embryonic stem cell associated LN-521 or LN-511 to explore if LN-221 does support their differentiation to cardiomyocytes. The results demonstrate that by using the specific LN-521 or LN-511 in combination with the highly heart muscle specific LN-221 as cell culture coatings, hES cells could be differentiated first to Islet-1 positive cardiomyocyte progenitor cells and, then after further culturing, to beating cardiomyocytes expressing, e.g., specific biomarkers like TnT. Methods of differentiating cardiac progenitor and mature cardiomyocyte cells from pluripotent stem cells are therefore controllable.

Example 2: Generation of Striated Muscle-Like Muscle Fiber

Pluripotent hESCs on LN-521 were maintained using a chemically defined maintenance medium, Nutristem (Stemgent), without the need of ROCK inhibitor. Nutristem contains low amount of bFGF (4 ng/ml) as compared to mTesR1 which contains unnecessary high (100 ng/ml) amount and bovine serum albumin (BSA). Prior to differentiation, $2\times10^5$ cells/cm$^2$ were seeded into wells coated overnight with a 50% mixture of LN-521 or LN-511 and LN-221 (provided by BioLamina).

Without being bound to any particular theory, the rationale is that LN-221 is the most abundant laminin expressed in the ultrathin basement membrane surrounding human heart muscle fibers The underlying LN-521 or LN-511 may promote cell attachment and proliferation, while LN-221 provides a natural niche for cardiomyocyte formation.

Cells were maintained for 4 days to achieve sub-confluence and at day 0 of differentiation, 12 UM of CHIR 99021 (Tocris) (a GSK-3 inhibitor) was added to differentiation media (RPMI/β27 minus insulin) to inhibit β-catenin phosphorylation which stimulates canonical Wnt signaling activities, and the cells were exposed to this differentiation media with GSK-3 inhibitor for 24 hours. The next day (day 1), media was changed to differentiation media (i.e. no inhibitor) and Brachyury positive cells are allowed to proliferate. On day 3, Wnt activities were inhibited by the addition of 5 UM of IWP 2 inhibitor (Tocris) to the differentiation media, this will promote cardiac mesodermal specification. On day 5, the medium was changed to basal medium (RPMI/β27) after which all subsequent medium changes were every 3 days. Striated muscle-like muscle fiber with regular beating will form by day 14. These cardiomyocytes are then stained with cardiac specific markers (Troponin T, Troponin I, MF-20) for fluorescence microscopy and flow cytometry. On top of full differentiation, specification of pluripotent cells to Islet-1 positive cardiac progenitors will complete at day 5 where these cells can be identified and maintained on LN-521.

Example 3. Stabilization and Expansion of Cardiomyocyte Progenitors as Exemplified by Islet-1 and NKX2.5 Positive Cells on LN-511 or LN-521

Maturation of cardiomyocyte progenitors can be stopped and maintained at their differentiation stage (e.g. islet-1 positivity) by placing them on either LN-511 or LN-521 matrix. At day 5 of the differentiation protocol, cells were dissociated with TrypLE buffer and re-plated into new LN-511/LN-521 coated wells with media containing GSK inhibitor which will enhance Wnt signaling, BMP inhibitor and Activin/Nodal inhibitor. Continual passaging of cells at sub-confluence ensures the stabilization and expansion of the highly homogenous progenitor cells.

Immunostaining of the progenitors showed that they are 99% positive for both islet-1 and NKX2.5 transcription factors. These cells can then be passaged at least 6 times such that the cells maintain 99% positivity for those two cardiomyocyte progenitor markers. These progenitors can also be long-term cryopreserved in mFreSR cryopreservation medium in liquid nitrogen. When required, cells can be thawed and they will readily proliferate or differentiate on laminins. These results are important as such progenitors probably render themselves best for cell transplantation in repair of damaged heart muscle.

The present disclosure has been described with reference to exemplary embodiments. Obviously, modifications and alterations will occur to others upon reading and understanding the preceding detailed description. It is intended that the present disclosure be construed as including all such modifications and alterations insofar that they come within the scope of the appended claims or the equivalents thereof.

The invention claimed is:

1. A method for obtaining cardiomyocyte progenitor cells from human pluripotent stem cells, comprising:
   (a) seeding the human pluripotent stem cells onto a substrate, wherein the substrate comprises a mixture of two laminins consisting of (i) recombinant laminin-521 (LN-521) or recombinant laminin-511 (LN-511) and (ii) recombinant laminin-221 (LN-221);
   (b) culturing the human pluripotent stem cells on the substrate in a differentiation medium containing a GSK-3 inhibitor to stimulate Wnt signaling to obtain brachyury positive cells;
   (c) culturing the brachyury positive cells on the substrate in a differentiation medium containing a Wnt inhibitor to inhibit Wnt signaling; and
   (d) removing the differentiation medium containing the Wnt inhibitor from step (c) and replacing with a basal medium to obtain cardiomyocyte progenitor cells that express Islet-1 and NKX2.5.

2. The method of claim 1, wherein the human pluripotent stem cells are cultured on the substrate in the differentiation medium containing the GSK-3 inhibitor for 1 day; or
   the brachyury positive cells are cultured on the substrate in the differentiation medium containing the Wnt inhibitor for 2 days.

3. The method of claim 1, wherein the human pluripotent stem cells are human embryonic stem cells.

4. The method of claim 1, wherein the human pluripotent stem cells are human induced pluripotent stem cells.

5. The method of claim 1, further comprising maintaining the cardiomyocyte progenitor cells on a culture plate coated with either LN-511 or LN-521 in a medium containing a GSK-3 inhibitor, wherein greater than 99% of the cardiomyocyte progenitor cells express Islet-1 and NKX2.5.

6. The method of claim 1, further comprising differentiating the cardiomyocyte progenitor cells to produce mature human cardiomyocyte cells that express Troponin T, myosin light chain for ventricular cells (MLC2v), and myosin sarcomere filament (MF-20) biomarkers.

7. The method of claim 1, wherein the GSK-3 inhibitor is CHIR 99021.

8. The method of claim 1, wherein the Wnt inhibitor is IWP 2.

* * * * *